(12) United States Patent
Hastings et al.

(10) Patent No.: US 8,473,067 B2
(45) Date of Patent: Jun. 25, 2013

(54) RENAL DENERVATION AND STIMULATION EMPLOYING WIRELESS VASCULAR ENERGY TRANSFER ARRANGEMENT

(75) Inventors: Roger Hastings, Maple Grove, MN (US); Anthony Vrba, Maple Grove, MN (US); Clara Davis, Minnetoka, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 40 days.

(21) Appl. No.: 13/157,844

(22) Filed: Jun. 10, 2011

(65) Prior Publication Data

US 2011/0307034 A1    Dec. 15, 2011

Related U.S. Application Data

(60) Provisional application No. 61/353,853, filed on Jun. 11, 2010.

(51) Int. Cl.
*A61N 1/00* (2006.01)

(52) U.S. Cl.
USPC .......................................................... 607/61

(58) Field of Classification Search
USPC ............... 607/61, 9, 62, 60, 59, 5, 46, 44, 40, 607/3, 2, 14, 116; 600/301, 507; 378/65
See application file for complete search history.

(56) References Cited

U.S. PATENT DOCUMENTS

| | | |
|---|---|---|
| 4,483,341 A | 11/1984 | Witteles |
| 4,649,936 A | 3/1987 | Ungar et al. |
| 5,251,634 A | 10/1993 | Weinberg |
| 5,653,684 A | 8/1997 | Laptewicz et al. |
| 5,755,682 A | 5/1998 | Knudson et al. |
| 5,830,222 A | 11/1998 | Makower |
| 5,947,977 A | 9/1999 | Slepian |
| 5,980,563 A | 11/1999 | Tu et al. |
| 6,014,590 A | 1/2000 | Whayne et al. |
| 6,068,638 A | 5/2000 | Makower |
| 6,078,839 A | 6/2000 | Carson |
| 6,093,166 A | 7/2000 | Knudson et al. |

(Continued)

FOREIGN PATENT DOCUMENTS

| | | |
|---|---|---|
| WO | WO9962413 | 12/1999 |
| WO | WO2006022790 | 3/2006 |

(Continued)

OTHER PUBLICATIONS

Stevenson, "Irrigated RF Ablation: Power Titration and Fluid Management for Optimal Safety Efficacy", 2005, 4 pages.

(Continued)

*Primary Examiner* — George Manuel
*Assistant Examiner* — Robert N Wieland
(74) *Attorney, Agent, or Firm* — Seager, Tufte & Wickhem, LLC

(57) ABSTRACT

Devices, systems, and methods provide for intravascular or extravascular delivery of renal denervation therapy and/or renal control stimulation therapy. Wireless vascular thermal transfer apparatuses and methods provide for one or both of production of current densities sufficient to ablate renal nerves and terminate renal sympathetic nerve activity, and production of current densities sufficient to induce endothelium dependent vasodilation of the renal artery bed. A common apparatus may be used for both renal ablation and control of renal function locally after renal denervation.

13 Claims, 15 Drawing Sheets

U.S. PATENT DOCUMENTS

| | | | |
|---|---|---|---|
| 6,102,908 | A | 8/2000 | Tu et al. |
| 6,106,477 | A | 8/2000 | Miesel et al. |
| 6,123,682 | A | 9/2000 | Knudson et al. |
| 6,129,725 | A | 10/2000 | Tu et al. |
| 6,159,225 | A | 12/2000 | Makower |
| 6,228,109 | B1 | 5/2001 | Tu et al. |
| 6,231,587 | B1 | 5/2001 | Makower |
| 6,248,126 | B1 | 6/2001 | Lesser et al. |
| 6,283,959 | B1 | 9/2001 | LaLonde |
| 6,292,695 | B1* | 9/2001 | Webster et al. ............... 607/14 |
| 6,350,248 | B1 | 2/2002 | Knudson et al. |
| 6,355,029 | B1 | 3/2002 | Joye |
| 6,361,519 | B1 | 3/2002 | Knudson et al. |
| 6,579,311 | B1 | 6/2003 | Makower |
| 6,685,732 | B2 | 2/2004 | Kramer |
| 6,802,857 | B1 | 10/2004 | Venugopalan |
| 6,847,848 | B2 | 1/2005 | Sterzer |
| 6,895,077 | B2 | 5/2005 | Karellas et al. |
| 6,905,494 | B2 | 6/2005 | Yon |
| 6,908,462 | B2 | 6/2005 | Joye |
| 6,929,009 | B2 | 8/2005 | Makower |
| 7,066,900 | B2 | 6/2006 | Botto et al. |
| 7,089,065 | B2 | 8/2006 | Westlund et al. |
| 7,162,303 | B2 | 1/2007 | Levin et al. |
| 7,203,537 | B2 | 4/2007 | Mower |
| 7,232,458 | B2 | 6/2007 | Saadat et al. |
| 7,238,184 | B2 | 7/2007 | Megerman et al. |
| 7,285,119 | B2 | 10/2007 | Stewart |
| 7,288,089 | B2 | 10/2007 | Yon |
| 7,323,006 | B2 | 1/2008 | Andreas et al. |
| 7,407,506 | B2 | 8/2008 | Makower et al. |
| 7,494,661 | B2 | 2/2009 | Sanders |
| 7,505,816 | B2 | 3/2009 | Schmeling et al. |
| 7,584,004 | B2 | 9/2009 | Caparso |
| 7,617,005 | B2 | 11/2009 | Demarais et al. |
| 7,620,451 | B2 | 11/2009 | Demarais et al. |
| 7,647,115 | B2 | 1/2010 | Levin et al. |
| 7,653,438 | B2 | 1/2010 | Deem et al. |
| 7,717,948 | B2 | 5/2010 | Demarais et al. |
| 7,846,172 | B2 | 12/2010 | Makower et al. |
| 7,853,333 | B2 | 12/2010 | Demarais et al. |
| 7,873,417 | B2 | 1/2011 | Demarais et al. |
| 2001/0007070 | A1 | 7/2001 | Stewart |
| 2002/0062146 | A1 | 5/2002 | Makower |
| 2003/0125721 | A1 | 7/2003 | Yon |
| 2003/0155539 | A1 | 8/2003 | Ginggen |
| 2003/0187368 | A1 | 10/2003 | Sata |
| 2003/0225442 | A1 | 12/2003 | Saadat |
| 2004/0073238 | A1 | 4/2004 | Makower |
| 2004/0147914 | A1 | 7/2004 | Kramer |
| 2004/0267250 | A1 | 12/2004 | Yon |
| 2005/0055073 | A1 | 3/2005 | Weber |
| 2005/0080374 | A1 | 4/2005 | Esch et al. |
| 2005/0209587 | A1 | 9/2005 | Joye |
| 2005/0252553 | A1 | 11/2005 | Ginggen |
| 2005/0256521 | A1 | 11/2005 | Kozel |
| 2006/0024564 | A1 | 2/2006 | Manclaw et al. |
| 2006/0041277 | A1 | 2/2006 | Deem et al. |
| 2006/0167106 | A1 | 7/2006 | Zhang |
| 2006/0184089 | A1 | 8/2006 | Makower et al. |
| 2007/0043338 | A1 | 2/2007 | Moll et al. |
| 2007/0106247 | A1 | 5/2007 | Burnett et al. |
| 2007/0129720 | A1 | 6/2007 | Demarais et al. |
| 2007/0129760 | A1 | 6/2007 | Demarais et al. |
| 2007/0129761 | A1 | 6/2007 | Demarais et al. |
| 2007/0135875 | A1 | 6/2007 | Demarais et al. |
| 2007/0173899 | A1* | 7/2007 | Levin et al. ............ 607/40 |
| 2007/0197896 | A1 | 8/2007 | Moll et al. |
| 2007/0208301 | A1 | 9/2007 | Evard |
| 2007/0225781 | A1 | 9/2007 | Saadat et al. |
| 2007/0250050 | A1 | 10/2007 | Lafontaine |
| 2007/0260281 | A1 | 11/2007 | Hastings |
| 2007/0265687 | A1 | 11/2007 | Deem et al. |
| 2007/0276461 | A1 | 11/2007 | Andreas et al. |
| 2007/0282302 | A1 | 12/2007 | Wachsman et al. |
| 2008/0004673 | A1 | 1/2008 | Rossing |
| 2008/0021408 | A1 | 1/2008 | Jacobsen |
| 2008/0039830 | A1 | 2/2008 | Munger et al. |
| 2008/0058836 | A1 | 3/2008 | Moll et al. |
| 2008/0082109 | A1 | 4/2008 | Moll et al. |
| 2008/0086072 | A1 | 4/2008 | Bonutti et al. |
| 2008/0097299 | A1 | 4/2008 | Andreas et al. |
| 2008/0108867 | A1 | 5/2008 | Zhou |
| 2008/0132450 | A1 | 6/2008 | Lee |
| 2008/0215117 | A1* | 9/2008 | Gross ............... 607/59 |
| 2008/0255642 | A1 | 10/2008 | Zarins et al. |
| 2008/0312673 | A1 | 12/2008 | Viswanathan et al. |
| 2009/0024194 | A1 | 1/2009 | Arcot-Krishnamurthy et al. |
| 2009/0036872 | A1 | 2/2009 | Fitzgerald |
| 2009/0036948 | A1 | 2/2009 | Levin et al. |
| 2009/0043372 | A1 | 2/2009 | Northrop |
| 2009/0062873 | A1 | 3/2009 | Wu et al. |
| 2009/0076409 | A1 | 3/2009 | Wu et al. |
| 2009/0131798 | A1 | 5/2009 | Minar et al. |
| 2009/0143640 | A1 | 6/2009 | Saadat et al. |
| 2009/0157161 | A1 | 6/2009 | Desai |
| 2009/0182360 | A1 | 7/2009 | Makower |
| 2009/0192558 | A1* | 7/2009 | Whitehurst et al. ............ 607/3 |
| 2009/0204170 | A1 | 8/2009 | Hastings |
| 2009/0210953 | A1 | 8/2009 | Moyer |
| 2009/0247966 | A1 | 10/2009 | Gunn et al. |
| 2009/0248012 | A1 | 10/2009 | Maor et al. |
| 2009/0270850 | A1 | 10/2009 | Zhou et al. |
| 2010/0114244 | A1* | 5/2010 | Manda et al. ............... 607/60 |
| 2010/0130836 | A1 | 5/2010 | Malchano et al. |
| 2010/0137860 | A1 | 6/2010 | Demarais et al. |
| 2010/0137952 | A1 | 6/2010 | Demarais et al. |
| 2010/0168731 | A1 | 7/2010 | Wu et al. |
| 2010/0168739 | A1 | 7/2010 | Wu et al. |
| 2010/0174169 | A1 | 7/2010 | Razavi |
| 2010/0174170 | A1 | 7/2010 | Razavi |
| 2010/0174282 | A1 | 7/2010 | Demarais et al. |
| 2010/0191112 | A1 | 7/2010 | Demarais et al. |
| 2010/0222851 | A1 | 9/2010 | Deem et al. |
| 2010/0222854 | A1 | 9/2010 | Demarais et al. |
| 2010/0249773 | A1 | 9/2010 | Clark et al. |
| 2010/0286684 | A1 | 11/2010 | Hata |
| 2010/0305036 | A1 | 12/2010 | Barnes |
| 2011/0040324 | A1 | 2/2011 | McCarthy et al. |
| 2011/0264086 | A1 | 10/2011 | Ingle |

FOREIGN PATENT DOCUMENTS

| | | |
|---|---|---|
| WO | WO2006041881 | 4/2006 |
| WO | WO2007035537 | 3/2007 |
| WO | WO2007078997 | 7/2007 |
| WO | WO2007086965 | 8/2007 |
| WO | WO2007103879 | 9/2007 |
| WO | WO2007103881 | 9/2007 |
| WO | WO2007121309 | 10/2007 |
| WO | WO2007146834 | 12/2007 |
| WO | WO2008003058 | 1/2008 |
| WO | WO2008061150 | 5/2008 |
| WO | WO2008061152 | 5/2008 |
| WO | WO2008070413 | 6/2008 |
| WO | WO2009121017 | 10/2009 |
| WO | WO2010078175 | 7/2010 |
| WO | WO2010129661 | 11/2010 |
| WO | WO2011091069 | 7/2011 |
| WO | WO2011130005 | 10/2011 |
| WO | WO2011139589 | 11/2011 |
| WO | WO2012019156 | 2/2012 |

OTHER PUBLICATIONS

Invitation to Pay Additional Fees dated Aug. 24, 2011 for PCT Application No. PCT/US2011/03257, 7 pages.

International Search Report and Written Opinion dated Oct. 10, 2011 for PCT Application No. PCT/US2011/03257, 15 pages.

* cited by examiner

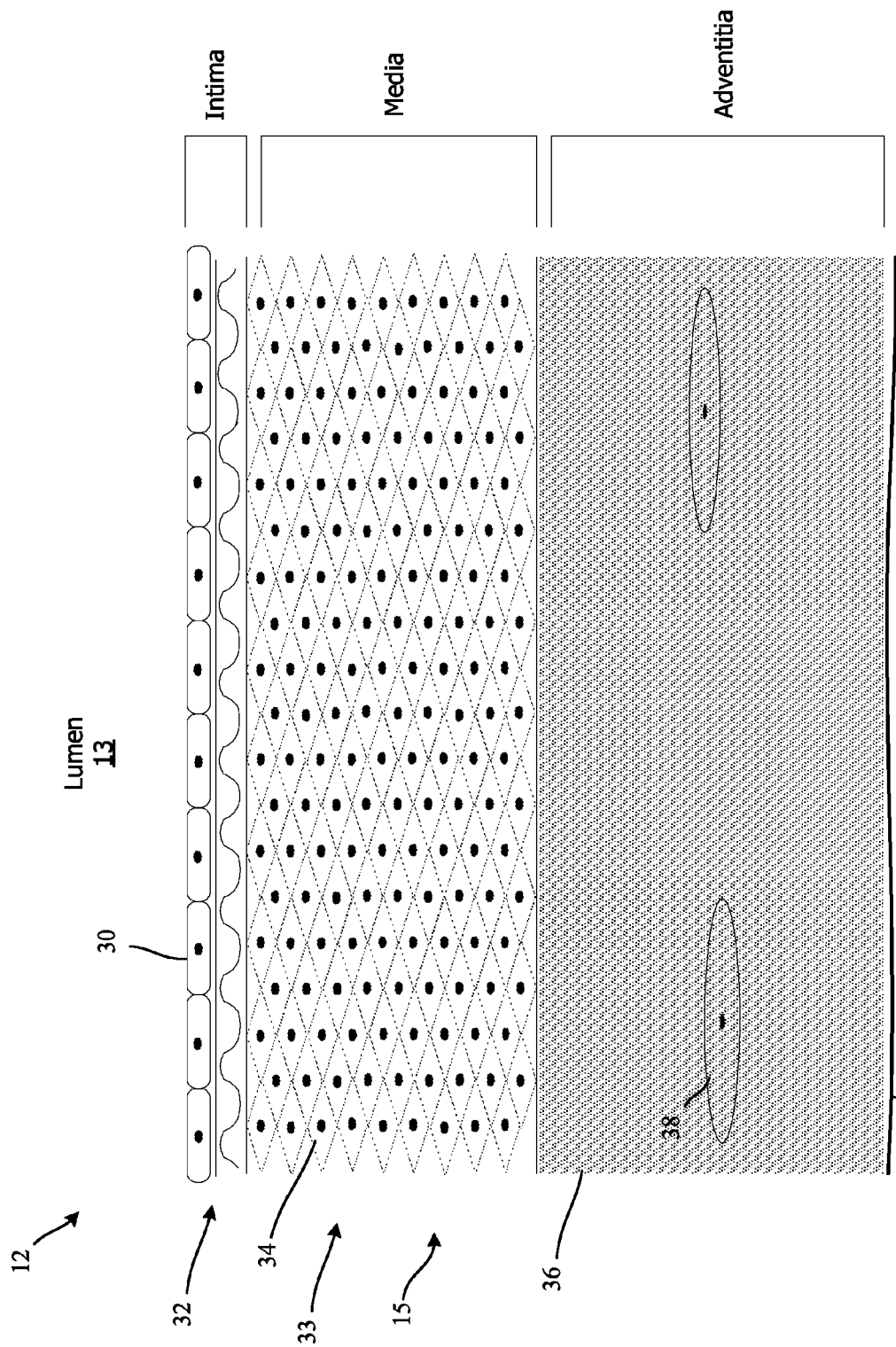

US 8,473,067 B2

RENAL DENERVATION AND STIMULATION EMPLOYING WIRELESS VASCULAR ENERGY TRANSFER ARRANGEMENT

RELATED PATENT DOCUMENTS

This application claims the benefit of Provisional Patent Application Ser. No. 61/353,853 filed on Jun. 11, 2010, to which priority is claimed under 35 U.S.C. §119(e), and which is incorporated herein by reference.

TECHNICAL FIELD

The present invention is related to systems and methods for improving cardiac and/or renal function, including renal stimulation and disruption and termination of renal sympathetic nerve activity.

BACKGROUND

The kidneys are instrumental in a number of body processes, including blood filtration, regulation of fluid balance, blood pressure control, electrolyte balance, and hormone production. One primary function of the kidneys is to remove toxins, mineral salts, and water from the blood to form urine. The kidneys receive about 20-25% of cardiac output through the renal arteries that branch left and right from the abdominal aorta, entering each kidney at the concave surface of the kidneys, the renal hilum.

Blood flows into the kidneys through the renal artery and the afferent arteriole, entering the filtration portion of the kidney, the renal corpuscle. The renal corpuscle is composed of the glomerulus, a thicket of capillaries, surrounded by a fluid-filled, cup-like sac called Bowman's capsule. Solutes in the blood are filtered through the very thin capillary walls of the glomerulus due to the pressure gradient that exists between the blood in the capillaries and the fluid in the Bowman's capsule. The pressure gradient is controlled by the contraction or dilation of the arterioles. After filtration occurs, the filtered blood moves through the efferent arteriole and the peritubular capillaries, converging in the interlobular veins, and finally exiting the kidney through the renal vein.

Particles and fluid filtered from the blood move from the Bowman's capsule through a number of tubules to a collecting duct. Urine is formed in the collecting duct and then exits through the ureter and bladder. The tubules are surrounded by the peritubular capillaries (containing the filtered blood). As the filtrate moves through the tubules and toward the collecting duct, nutrients, water, and electrolytes, such as sodium and chloride, are reabsorbed into the blood.

The kidneys are innervated by the renal plexus which emanates primarily from the aorticorenal ganglion. Renal ganglia are formed by the nerves of the renal plexus as the nerves follow along the course of the renal artery and into the kidney. The renal nerves are part of the autonomic nervous system which includes sympathetic and parasympathetic components. The sympathetic nervous system is known to be the system that provides the bodies "fight or flight" response, whereas the parasympathetic nervous system provides the "rest and digest" response. Stimulation of sympathetic nerve activity triggers the sympathetic response which causes the kidneys to increase production of hormones that increase vasoconstriction and fluid retention. This process is referred to as the renin-angiotensin-aldosterone-system (RAAS) response to increased renal sympathetic nerve activity.

In response to a reduction in blood volume, the kidneys secrete renin, which stimulates the production of angiotensin. Angiotensin causes blood vessels to constrict, resulting in increased blood pressure, and also stimulates the secretion of the hormone aldosterone from the adrenal cortex. Aldosterone causes the tubules of the kidneys to increase the reabsorption of sodium and water, which increases the volume of fluid in the body and blood pressure.

Congestive heart failure (CHF) is a condition that has been linked to kidney function. CHF occurs when the heart is unable to pump blood effectively throughout the body. When blood flow drops, renal function degrades because of insufficient perfusion of the blood within the renal corpuscles. The decreased blood flow to the kidneys triggers an increase in sympathetic nervous system activity (i.e., the RAAS becomes too active) that causes the kidneys to secrete hormones that increase fluid retention and vasorestriction. Fluid retention and vasorestriction in turn increases the peripheral resistance of the circulatory system, placing an even greater load on the heart, which diminishes blood flow further. If the deterioration in cardiac and renal functioning continues, eventually the body becomes overwhelmed, and an episode of heart failure decompensation occurs, often leading to hospitalization of the patient.

Hypertension is a chronic medical condition in which the blood pressure is elevated. Persistent hypertension is a significant risk factor associated with a variety of adverse medical conditions, including heart attacks, heart failure, arterial aneurysms, and strokes. Persistent hypertension is a leading cause of chronic renal failure. Hyperactivity of the sympathetic nervous system serving the kidneys is associated with hypertension and its progression. Deactivation of nerves in the kidneys via renal denervation can reduce blood pressure, and may be a viable treatment option for many patients with hypertension who do not respond to conventional drugs.

SUMMARY

Devices, systems, and methods of the present invention are directed to renal denervation. Devices, systems, and methods of the present invention are directed to renal stimulation for renal function modification. Devices, systems, and methods of the present invention are directed to combined renal denervation and renal stimulation using a common implantable apparatus.

Embodiments of the present invention are directed to apparatuses and methods for intravascular or extravascular delivery of a denervation therapy to a renal artery of a patient. Embodiments of the present invention are directed to apparatuses and methods for intravascular or extravascular delivery of renal stimulation therapy to a renal artery of a patient, with or without delivery of denervation therapy.

Embodiments of the invention are directed to apparatuses and methods that stimulate and control the potential of the endothelium layer of the renal artery. Embodiments of the invention are directed to apparatuses and methods that stimulate and control the potential of the internal elastic membrane of the endothelium of the renal artery. Embodiments of the invention are directed to apparatuses and methods for producing current densities sufficient to hyperpolarize endothelium cells and cause production and release of nitric oxide into blood flowing through the renal artery, the amount of released nitric oxide sufficient to cause vasodilation of the renal artery bed. Embodiments of the invention are directed to controlling renal function locally after renal denervation.

Embodiments of the invention are directed to apparatuses and methods that provide for both production of current densities sufficient to ablate renal nerves and terminate renal sympathetic nerve activity, and production of current densities sufficient to induce endothelium dependent vasodilation of the renal artery bed. A common apparatus may be used for both renal ablation and control of renal function locally after renal denervation.

In accordance with embodiments of the invention, an apparatus for intravascular delivery of one or both of denervation and stimulation therapy to a renal artery of a patient includes a stent dimensioned for deployment within the renal artery and adapted for chronic fixation within the renal artery. An electrode arrangement and an antenna arrangement are supported by the stent. The antenna arrangement is configured to receive energy from a power source external of the renal artery. The electrode and antenna arrangements, in a first configuration, are operative to produce current densities sufficient to ablate renal nerves and terminate renal sympathetic nerve activity. In a second configuration, the electrode and antenna arrangements are operative to produce current densities sufficient to induce endothelium dependent vasodilation of the renal artery bed. The power source for at least the second configuration supplies energy to the antenna arrangement other than by way of a percutaneous electrical lead. In some embodiments, the power source for the first configuration supplies energy to the electrode arrangement via a percutaneous lead.

In some embodiments, the electrode and antenna arrangements, in the second configuration, may be operated to produce current densities sufficient to induce endothelium dependent vasodilation of the renal artery bed distal to the stent. In other embodiments, the electrode and antenna arrangements, in the second configuration, are operative to produce current densities sufficient to hyperpolarize endothelium adjacent the stent and cause production and release of nitric oxide into blood flowing past the stent, the amount of released nitric oxide sufficient to cause vasodilation of the renal artery bed distal to the stent.

According to other embodiments, an apparatus for intravascular delivery of denervation therapy to a renal artery of a patient includes a stent dimensioned for deployment within the renal artery and adapted for chronic fixation within the renal artery. An electrode arrangement is supported by the stent and comprises an anode contact arranged to electrically couple to an inner wall of the renal artery and electrically insulated from blood passing through a lumen of the stent. The electrode arrangement includes a cathode contact arranged to electrically coupled with blood passing through the lumen of the stent and electrically insulated from the inner wall of the renal artery. An antenna arrangement is supported by the stent and electrically coupled to the electrode arrangement, the antenna arrangement configured to receive energy from a power source external of the renal artery. The electrode and antenna arrangements are configured to produce current densities sufficient to ablate renal nerves and terminate renal sympathetic nerve activity, and the power source supplies energy to the antenna arrangement other than by way of a percutaneous electrical lead.

In accordance with further embodiments, an apparatus for intravascular delivery of stimulation therapy to a renal artery of a patient includes a stent dimensioned for deployment within the renal artery and adapted for chronic fixation within the renal artery. An electrode arrangement is supported by the stent and comprises an anode contact arranged to electrically couple to an inner wall of the renal artery and electrically insulated from blood passing through a lumen of the stent. A cathode contact is arranged to electrically couple with blood passing through the lumen of the stent and electrically insulated from the inner wall of the renal artery. An antenna arrangement is supported by the stent and electrically coupled to the electrode arrangement, the antenna arrangement configured to receive energy from a power source external of the renal artery. The electrode and antenna arrangements are configured to produce current densities sufficient to induce endothelium dependent vasodilation of the renal artery bed, and the power source supplies energy to the antenna arrangement other than by way of a percutaneous electrical lead.

In some embodiments, the power source comprises a power source external of the patient. In other embodiments, the power source comprises an implantable power source. The power source may comprise an implantable power source configured to wirelessly couple energy to the antenna arrangement.

For example, the power source may include a patient-external power source and an implantable power source. The patient-external power source is configured to couple energy to the implantable power source, and the implantable power source is configured to wirelessly couple energy to the antenna arrangement.

By way of further example, the power source may include a first implantable power source and a second implantable power source. The first implantable power source may be configured to transmit power to the second implantable power source, and the second implantable power source may be configured to wirelessly couple energy to the antenna arrangement.

In some embodiments, the antenna arrangement comprises an inductive coil. In other embodiments, the stent comprises at least two struts, and the antenna arrangement comprises at least the two struts.

Circuitry may be coupled to the antenna and electrode arrangements. The circuitry may be configured to receive current induced in the antenna arrangement and store a charge developed using the induced current. For example, an electronics module may be supported by the stent and coupled to the antenna and electrode arrangements. The electronics module may include rectifier circuitry and a storage capacitor. The rectifier circuitry is configured to receive current induced in the antenna arrangement and the storage capacitor is configured to store a charge developed using current received from the rectifier circuitry.

In accordance with various embodiments, the power source comprises an implantable structure configured for deployment within a renal vein at a renal vein location proximate a location of the stent within the renal artery. A transmitter is supported by the implantable structure within the renal vein and configured to transmit energy to the antenna arrangement of the renal artery stent via a transvascular pathway. The power source may include an implantable extrathoracic power supply and a lead electrically coupling the power supply and the transmitter. The implantable structure may comprise a stent configured for chronic fixation within the renal vein.

In various embodiments, a controller and a sensing circuit are configured for sensing cardiac activity, and the controller and sensing circuit are supported by the stent disposed in the renal artery. The controller is configured to transmit stimulation pulses to the renal artery wall via the electrode arrangement in synchrony with sensed cardiac events. In other embodiments, a controller and a sensing circuit are configured for sensing cardiac activity, and are respectively supported by the implantable structure disposed in the renal vein. The controller is configured to transmit energy pulses to the antenna arrangement of the renal artery stent in synchrony with sensed cardiac events.

In further embodiments, the implantable renal apparatus is configured to deliver repeated renal nerve ablation in response to detection of re-innervation of the renal artery. One or more sensors may be configured for sensing one or more physiologic parameters that facilitate detection of renal sympathetic nerve activity associated with re-innervation of the renal artery.

In other embodiments, the implantable renal apparatus is configured to deliver repeated renal stimulation in response to detection of one or more physiologic parameters influenced or modulated by one or more renal functions. One or more sensors may be configured for sensing the physiologic parameters that facilitate monitoring of one or more renal functions and detection of changes in renal functions that necessitate remedial renal stimulation therapy.

In some embodiments, a portable power source is configured for transport by an ambulatory patient. The portable power source is configured and controlled to couple energy to the stent in accordance with a predetermined renal artery stimulation therapy.

In accordance with various embodiments, an apparatus for delivering denervation therapy to a renal artery of a patient includes a support structure dimensioned for deployment at the renal artery and configured for chronic fixation at the renal artery. A thermal transfer arrangement is supported by the support structure and comprises one or more thermoelectric elements configured to thermally couple to the renal artery and capable of operating in a hyperthermic configuration. Power circuitry is supported by the support structure and coupled to the thermal transfer arrangement. The power circuit comprises a receiver configured to receive energy from a power source external of the renal artery, the power source supplying energy to the receiver other than by a percutaneous lead.

A control circuit is supported by the support structure and coupled to the power circuitry. The control circuit, in the hyperthermic configuration, is configured to coordinate delivery of hyperthermic ablation therapy to ablate renal nerves and terminate renal sympathetic nerve activity. In some embodiments, one or more of the thermoelectric elements are capable of operating in a hypothermic configuration and situated on the thermal transfer arrangement to cool non-targeted tissues of the renal artery.

According to other embodiments, an apparatus for delivering denervation therapy to a renal artery of a patient includes a support structure dimensioned for deployment at the renal artery and configured for chronic fixation at the renal artery. A thermal transfer arrangement is supported by the support structure and comprises one or more thermoelectric elements configured to thermally couple to the renal artery and capable of operating in a hypothermic configuration. Power circuitry is supported by the support structure and coupled to the thermal transfer arrangement. The power circuit comprises a receiver configured to receive energy from a power source external of the renal artery, the power source supplying energy to the receiver other than by a percutaneous lead. A control circuit is supported by the support structure and coupled to the power circuitry. The control circuit, in the hypothermic configuration, is configured to coordinate delivery of hypothermic ablation therapy to freeze renal nerves and terminate renal sympathetic nerve activity.

In accordance with further embodiments, an apparatus for delivering denervation therapy to a renal artery of a patient includes a support structure dimensioned for deployment at the renal artery and configured for chronic fixation at the renal artery. A thermal transfer arrangement is supported by the support structure and comprises one or more thermoelectric elements configured to thermally couple to the renal artery and capable of selectively operating in a hyperthermic configuration and a hypothermic configuration. The one or more thermoelectric elements comprise solid-state thermoelectric elements. For example, the one or more thermoelectric elements comprise Peltier elements.

Power circuitry is supported by the support structure and coupled to the thermal transfer arrangement, the power circuit comprising a receiver configured to receive energy from a power source external of the renal artery. The power source supplies energy to the receiver other than by a percutaneous lead. A control circuit is supported by the support structure and coupled to the power circuitry. The control circuit, in the hypothermic configuration, is operative to coordinate delivery of hypothermic ablation therapy to freeze renal nerves and terminate renal sympathetic nerve activity. The control circuit, in the hyperthermic configuration, is configured to coordinate delivery of hyperthermic therapy to at least heat renal nerves to above freezing.

The control circuit may be configured to deliver a sequence of freeze/thaw therapy cycles. The control circuit, in the hyperthermic configuration, may be configured to coordinate delivery of a hyperthermic ablation therapy to ablate renal nerves and terminate renal sympathetic nerve activity. The control circuit, in a monitoring configuration in which hypothermic and hypothermic therapy delivery are disabled, may be operative to coordinate monitoring of at least one physiologic parameter that facilitates detection of renal sympathetic nerve activity associated with re-innervation of the renal artery and/or changes in one or more renal functions.

The support structure may be configured for intravascular or extravascular chronic deployment within the renal artery. For example, the implantable structure may comprise a stent. The power source may comprise a patient-external power source, and implantable power source, or a combination of patient-external and implantable power sources.

In some embodiments, the power source may comprise an implantable structure configured for deployment within a renal vein at a renal vein location proximate a location of the support structure within the renal artery. A transmitter is supported by the implantable structure and configured to transmit energy to the receiver via a transvascular pathway.

In other embodiments, the power source comprises an implantable structure configured for deployment within a renal vein at a renal vein location proximate a location of the support structure within the renal artery. A transmitter is supported by the implantable structure and configured to transmit energy to the receiver via a transvascular pathway. The power source further comprises an implantable extrathoracic power supply and a lead electrically coupling the power supply and the transmitter.

According to further embodiments, a controller and a sensing circuit are configured for sensing cardiac activity. The controller and sensing circuit are supported by the support structure. In some embodiments, the controller is configured to control transfer of thermal energy to the renal artery wall via the thermal transfer arrangement in synchrony with sensed cardiac events. In other embodiments, the controller is configured to control transmission of energy pulses to the receiver of the support structure within the renal artery in synchrony with sensed cardiac events.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

DESCRIPTION OF THE DRAWINGS

FIG. 3A illustrates various tissue layers of the wall of the renal artery;

Figure 1:
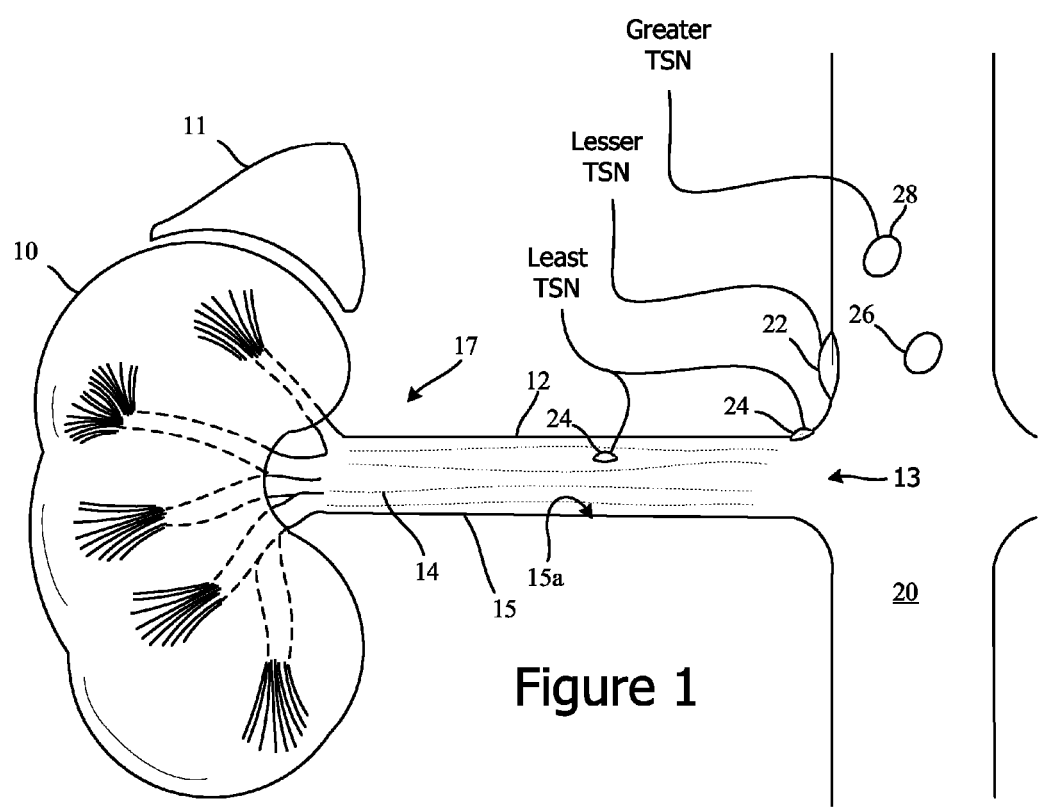
FIG. 1 is an illustration of a right kidney and renal vasculature including a renal artery branching laterally from the abdominal aorta.

While the invention is amenable to various modifications and alternative forms, specifics thereof have been shown by way of example in the drawings and will be described in detail. It is to be understood, however, that the intention is not to limit the invention to the particular embodiments described. On the contrary, the intention is to cover all modifications, equivalents, and alternatives falling within the scope of the invention as defined by the appended claims.

DETAILED DESCRIPTION

In the following description, references are made to the accompanying drawings which illustrate various embodiments of the invention. It is to be understood that other embodiments may be utilized, and structural and functional changes may be made to these embodiments without departing from the scope of the present invention.

Recent human clinical trials have indicated that sympathetic denervation of the kidneys, via ablation of nerve fibers that run along the adventitia of the renal artery, can significantly reduce blood pressure in patients with hypertension that is refractory to drug therapy. It has been hypothesized that this procedure may also be a potent therapy for congestive heart failure, because ablation of the renal nerves reduces sodium reabsorption and reduces production of the enzyme renin by the kidney, in addition to increasing blood flow through the kidney and diuresis via dilation of the renal arteriole bed. However, it is understood that control of vascular function has multiple sources, only one of which being the autonomous nervous system. Local sources of control include nitric oxide (NO) production in the endothelial cells lining the renal artery system, serum carbon dioxide concentration that varies with tissue metabolism, blood pH and temperature.

It is believed that all of these sources have a common effect on the cells in the renal vasculature, namely control of the vascular cell membrane potential. For example, hyperpolarization of smooth muscle (i.e., increase in the magnitude of the membrane potential) causes relaxation and vasodilation, while depolarization of the membrane potential causes vasoconstriction.

Hyperpolarization or depolarization may be accomplished by altering ionic concentrations in the arterial wall extracellular space. For example, injection of negative charge through a pacing electrode cathode depolarizes myocytes and causes a local contraction that propagates throughout the heart. Conversely, reducing blood pH by increased production of carbon dioxide during increased metabolic activity hyperpolarizes neighboring vascular cells and causes smooth muscle cell relaxation and vasodilation, thus providing more blood and oxygen to fuel the increased metabolism.

Local hyperpolarization of endothelial cells propagates down a vascular bed and causes more global vasodilation of the artery bed distal of the local hyperpolarization. This is believed to be due to increased production of NO in the endothelial cells in response to an increase in membrane potential. The NO is carried downstream by the blood flow, resulting in dilation of the distal bed of arterioles. In addition, hyperpolarization may be conducted directly through tight junctions between endothelium cells and through gap junctions to smooth muscle cells.

Embodiments of the invention include a wireless intravascular or extravascular electrode (e.g., a stent electrode) or thermal generator (e.g., stent with thermoelectric elements) placed in or on the renal artery at the time of renal denervation. Stimulation power is preferably transmitted to the stent electrode or thermal generator from a transmit antenna in the adjacent renal vein. The renal vein transmit antenna may be powered using a patient-external device, an implantable medical device via wired or wireless connection, or both power resources. Some embodiments include transvascular implementations with stimulation applied to leads in the renal vein that flows across the vein wall to the nerves adjacent the renal artery. Alternative wireless approaches provide a transmitter in the renal vein that transmits RF power over a short distance to a wireless stent electrode or thermal generator implanted in the renal artery for nerve stimulation or thermal therapy. In some embodiments, renal nerves are ablated, and stimulation current or thermal therapy is thereafter provided to the endothelial cells adjacent the stent to induce endothelium dependent vasodilatation of the renal artery bed to facilitate renal function control and modification.

In some embodiments, an intravascular or extravascular electrode arrangement or thermal generator is configured to provide direct thermal denervation to the renal artery. Various embodiments involve inducing currents in a heating coil and thermally ablating renal artery wall tissue along the length of the heating coil using heat generated in the coil. In other embodiments, the electrode arrangement may be configured to deliver conductive RF heating ablation denervation therapy to the renal artery.

According to some embodiments, an intravascular or extravascular wireless electrode arrangement, such as a stent, is dimensioned for deployment at a proximal renal artery location biased more toward the patient's abdominal aorta than the patient's kidney. Electrode and antenna arrangements of the wireless electrode stent may be configured to produce current densities sufficient to induce endothelium dependent vasodilation of the renal artery bed distal to the stent. For example, the electrode and antenna arrangements of the wireless electrode stent may be configured to produce current densities sufficient to hyperpolarize endothelium adjacent the stent and cause production and release of nitric oxide into blood flowing past the stent. The amount of released nitric oxide is preferably sufficient to cause vasodilation of the renal artery bed distal to the stent.

Apparatuses according to embodiments of the invention may be configured to deliver repeated renal nerve ablation in response to detection of renal nerve regeneration or re-innervation. A sensor may be configured for sensing a physiologic parameter that facilitates detection of renal sympathetic nerve activity associated with renal nerve re-innervation. Repeated renal nerve ablation may be performed based on the sensed physiologic parameter, such as on an ambulatory basis using a portable power source configured and controlled to couple energy to the wireless electrode stent in accordance with a predetermined renal artery stimulation therapy.

The following description with regard to FIGS. 1-3C provides anatomical context for embodiments of the invention that are directed to methods and apparatuses for implementing renal denervation and/or renal stimulation, it being understood that various embodiments may be implemented for deployment and/or treatment for other organs and structures of the body. FIG. 1 is an illustration of a right kidney 10 and renal vasculature including a renal artery 12 branching laterally from the abdominal aorta 20. In FIG. 1, only the right kidney 10 is shown for purposes of simplicity of explanation, but reference will be made herein to both right and left kidneys and associated renal vasculature and nervous system structures, all of which are contemplated within the context of embodiments of the present invention. The renal artery 12 is purposefully shown to be disproportionately larger than the right kidney 10 and abdominal aorta 20 in order to facilitate discussion of various features and embodiments of the present disclosure.

The right and left kidneys are supplied with blood from the right and left renal arteries that branch from respective right and left lateral surfaces of the abdominal aorta 20. Each of the right and left renal arteries is directed across the crus of the diaphragm, so as to form nearly a right angle with the abdominal aorta 20. The right and left renal arteries extend generally from the abdominal aorta 20 to respective renal sinuses proximate the hilum 17 of the kidneys, and branch into segmental arteries and then interlobular arteries within the kidney 10. The interlobular arteries radiate outward, penetrating the renal capsule and extending through the renal columns between the renal pyramids. Typically, the kidneys receive about 20% of total cardiac output which, for normal persons, represents about 1200 mL of blood flow through the kidneys per minute.

The primary function of the kidneys is to maintain water and electrolyte balance for the body by controlling the production and concentration of urine. In producing urine, the kidneys excrete wastes such as urea and ammonium. The kidneys also control reabsorption of glucose and amino acids, and are important in the production of hormones including vitamin D, renin and erythropoietin.

An important secondary function of the kidneys is to control metabolic homeostasis of the body. Controlling hemostatic functions include regulating electrolytes, acid-base balance, and blood pressure. For example, the kidneys are responsible for regulating blood volume and pressure by adjusting volume of water lost in the urine and releasing erythropoietin and renin, for example. The kidneys also regulate plasma ion concentrations (e.g., sodium, potassium, chloride ions, and calcium ion levels) by controlling the quantities lost in the urine and the synthesis of calcitrol. Other hemostatic functions controlled by the kidneys include stabilizing blood pH by controlling loss of hydrogen and bicarbonate ions in the urine, conserving valuable nutrients by preventing their excretion, and assisting the liver with detoxification.

Also shown in FIG. 1 is the right suprarenal gland 11, commonly referred to as the right adrenal gland. The suprarenal gland 11 is a star-shaped endocrine gland that rests on top of the kidney 10. The primary function of the suprarenal glands (left and right) is to regulate the stress response of the body through the synthesis of corticosteroids and catecholamines, including cortisol and adrenaline (epinephrine), respectively. Encompassing the kidneys 10, suprarenal glands 11, renal vessels 12, and adjacent perirenal fat is the renal fascia, e.g., Gerota's fascia, (not shown), which is a fascial pouch derived from extraperitoneal connective tissue.

The autonomic nervous system of the body controls involuntary actions of the smooth muscles in blood vessels, the digestive system, heart, and glands. The autonomic nervous system is divided into the sympathetic nervous system and the parasympathetic nervous system. In general terms, the parasympathetic nervous system prepares the body for rest by lowering heart rate, lowering blood pressure, and stimulating digestion. The sympathetic nervous system effectuates the body's fight-or-flight response by increasing heart rate, increasing blood pressure, and increasing metabolism.

In the autonomic nervous system, fibers originating from the central nervous system and extending to the various ganglia are referred to as preganglionic fibers, while those extending from the ganglia to the effector organ are referred to as postganglionic fibers. Activation of the sympathetic nervous system is effected through the release of adrenaline (epinephrine) and to a lesser extent norepinephrine from the suprarenal glands 11. This release of adrenaline is triggered by the neurotransmitter acetylcholine released from preganglionic sympathetic nerves.

Figure 2A:
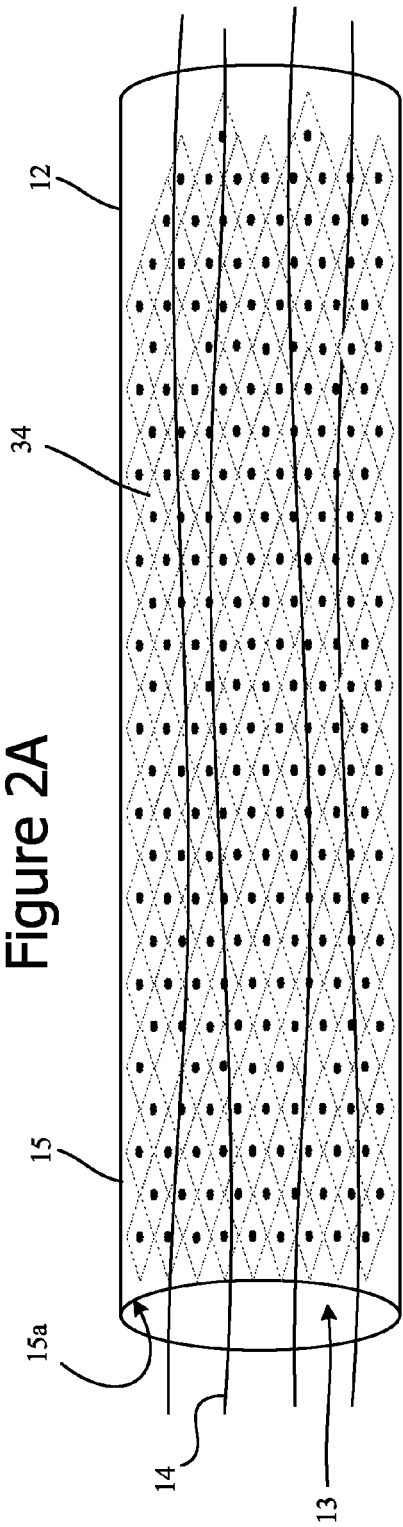
FIGS. 2A and 2B illustrate sympathetic innervation of the renal artery.
Figure 2B:
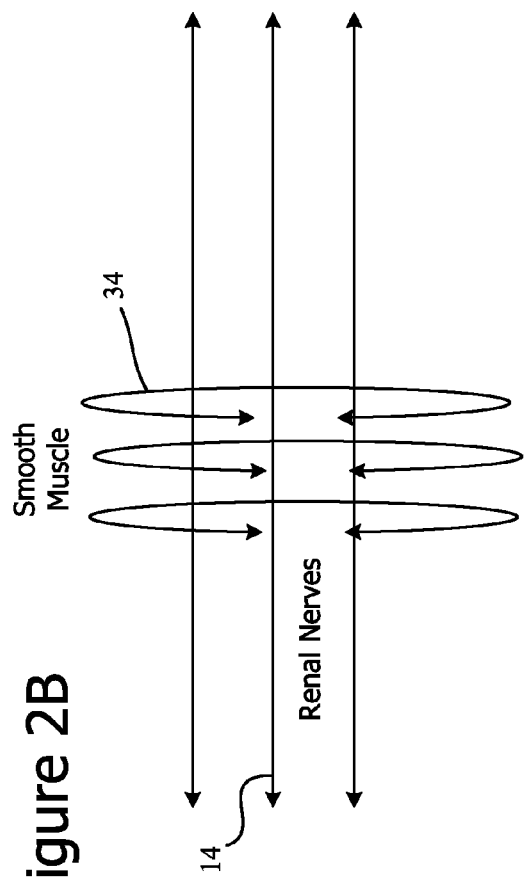

The kidneys and ureters (not shown) are innervated by the renal nerves 14. FIGS. 1 and 2A-2B illustrate sympathetic innervation of the renal vasculature, primarily innervation of the renal artery 12. The primary functions of sympathetic innervation of the renal vasculature include regulation of renal blood flow and pressure, stimulation of renin release, and direct stimulation of water and sodium ion reabsorption.

Most of the nerves innervating the renal vasculature are sympathetic postganglionic fibers arising from the superior mesenteric ganglion 26. The renal nerves 14 extend generally axially along the renal arteries 12, enter the kidneys 10 at the hilum 17, follow the branches of the renal arteries 12 within the kidney 10, and extend to individual nephrons. Other renal ganglia, such as the renal ganglia 24, superior mesenteric ganglion 26, the left and right aorticorenal ganglia 22, and celiac ganglia 28 also innervate the renal vasculature. The celiac ganglion 28 is joined by the greater thoracic splanchnic nerve (greater TSN). The aorticorenal ganglia 26 is joined by the lesser thoracic splanchnic nerve (lesser TSN) and innervates the greater part of the renal plexus.

Sympathetic signals to the kidney 10 are communicated via innervated renal vasculature that originates primarily at spinal segments T10-T12 and L1. Parasympathetic signals originate primarily at spinal segments S2-S4 and from the medulla oblongata of the lower brain. Sympathetic nerve traffic travels through the sympathetic trunk ganglia, where some may synapse, while others synapse at the aorticorenal ganglion 22 (via the lesser thoracic splanchnic nerve, i.e., lesser TSN) and the renal ganglion 24 (via the least thoracic splanchnic nerve, i.e., least TSN). The postsynaptic sympathetic signals then travel along nerves 14 of the renal artery 12 to the kidney 10. Presynaptic parasympathetic signals travel to sites near the kidney 10 before they synapse on or near the kidney 10.

With particular reference to FIG. 2A, the renal artery 12, as with most arteries and arterioles, is lined with smooth muscle 34 that controls the diameter of the renal artery lumen 13. Smooth muscle, in general, is an involuntary non-striated muscle found within the media layer of large and small arteries and veins, as well as various organs. The glomeruli of the kidneys, for example, contain a smooth muscle-like cell called the mesangial cell. Smooth muscle is fundamentally different from skeletal muscle and cardiac muscle in terms of structure, function, excitation-contraction coupling, and mechanism of contraction.

Smooth muscle cells can be stimulated to contract or relax by the autonomic nervous system, but can also react on stimuli from neighboring cells and in response to hormones and blood borne electrolytes and agents (e.g., vasodilators or vasoconstrictors). Specialized smooth muscle cells within the afferent arteriole of the juxtaglomerular apparatus of kidney 10, for example, produces renin which activates the angiotension II system.

The renal nerves 14 innervate the smooth muscle 34 of the renal artery wall 15 and extend lengthwise in a generally axial or longitudinal manner along the renal artery wall 15. The smooth muscle 34 surrounds the renal artery circumferentially, and extends lengthwise in a direction generally transverse to the longitudinal orientation of the renal nerves 14, as is depicted in FIG. 2B.

The smooth muscle 34 of the renal artery 12 is under involuntary control of the autonomic nervous system. An increase in sympathetic activity, for example, tends to contract the smooth muscle 34, which reduces the diameter of the renal artery lumen 13 and decreases blood perfusion. A decrease in sympathetic activity tends to cause the smooth muscle 34 to relax, resulting in vessel dilation and an increase in the renal artery lumen diameter and blood perfusion. Conversely, increased parasympathetic activity tends to relax the smooth muscle 34, while decreased parasympathetic activity tends to cause smooth muscle contraction.

Figure 3B:
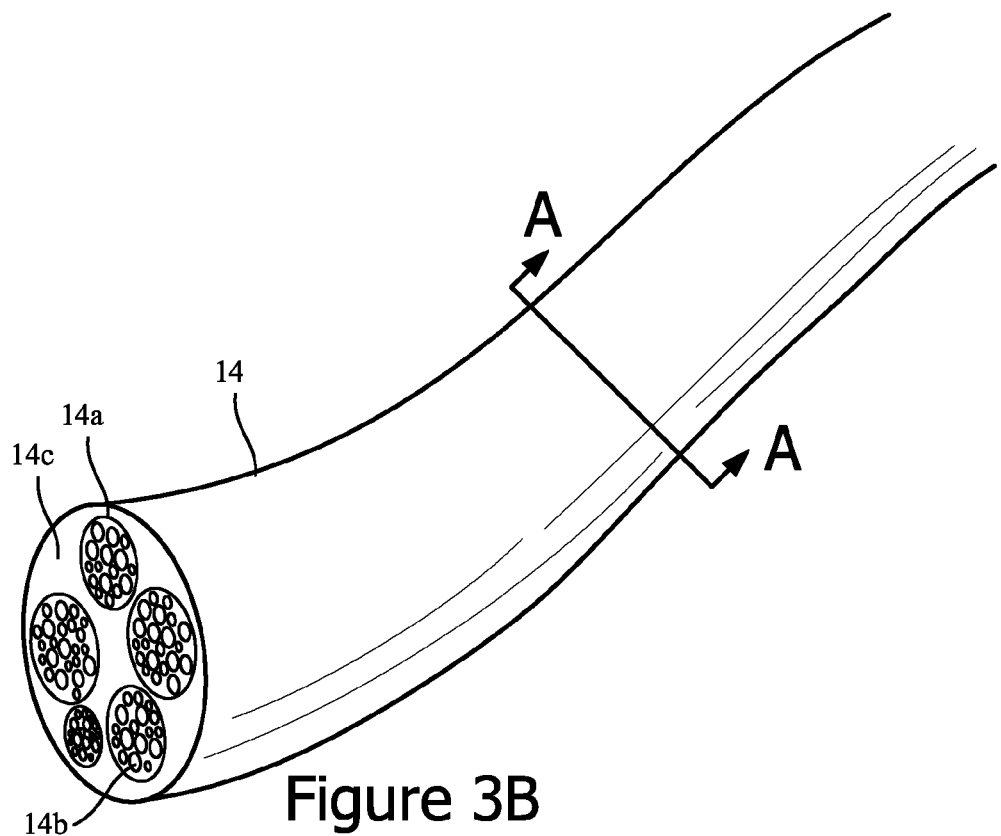
FIGS. 3B and 3C illustrate a portion of a renal nerve.
Figure 3C:
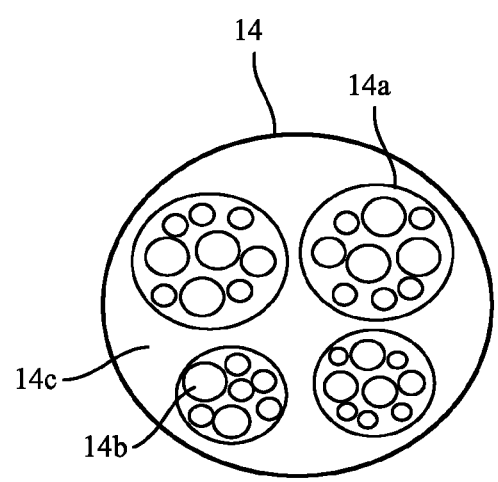

FIG. 3A shows a segment of a longitudinal cross-section through a renal artery, and illustrates various tissue layers of the wall 15 of the renal artery 12. The innermost layer of the renal artery 12 is the endothelium 30, which is the innermost layer of the intima 32 and is supported by an internal elastic membrane. The endothelium 30 is a single layer of cells that contacts the blood flowing though the vessel lumen 13. Endothelium cells are typically polygonal, oval, or fusiform, and have very distinct round or oval nuclei. Cells of the endothelium 30 are involved in several vascular functions, including control of blood pressure by way of vasoconstriction and vasodilation, blood clotting, and acting as a barrier layer between contents within the lumen 13 and surrounding tissue, such as the membrane of the intima 32 separating the intima 32 from the media 34, and the adventitia 36. The membrane or maceration of the intima 32 is a fine, transparent, colorless structure which is highly elastic, and commonly has a longitudinal corrugated pattern.

Adjacent the intima 32 is the media 33, which is the middle layer of the renal artery 12. The media is made up of smooth muscle 34 and elastic tissue. The media 33 can be readily identified by its color and by the transverse arrangement of its fibers. More particularly, the media 33 consists principally of bundles of smooth muscle fibers 34 arranged in a thin plate-like manner or lamellae and disposed circularly around the arterial wall 15. The outermost layer of the renal artery wall 15 is the adventitia 36, which is made up of connective tissue. The adventitia 36 includes fibroblast cells 38 that play an important role in wound healing.

A renal nerve 14 is shown proximate the adventitia 36 and extending longitudinally along the renal artery 12. The main trunk of the renal nerves 14 generally lies at or adjacent the adventitia of the renal artery 12, with certain branches coursing into the media to enervate the renal artery smooth muscle. For example, renal nerves may be situated in the adventitia proximate the outer wall of the renal artery (e.g., tunica adventitia) or within the vasa vasorum, such as the vasa vasorum externae.

A variety of conventional renal denervation approaches have been developed to treat refractory hypertension and heart failure. However, renal functions are only partially controlled by the autonomic nervous system, to which conventional renal denervation approaches are directed. Local factors such as pH, serum carbon dioxide concentration, certain chemicals such as nitric oxide (NO) and temperature further regulate renal function and vascular tone, even after the renal nerves have been ablated.

Embodiments of the invention are directed to apparatuses and methods that stimulate and control the potential of the endothelium layer of the renal artery. Embodiments of the invention are directed to apparatuses and methods that stimulate and control the potential of the internal elastic membrane of the endothelium of the renal artery. Embodiments of the invention are directed to apparatuses and methods for producing current densities sufficient to hyperpolarize endothelium cells and cause production and release of nitric oxide into blood flowing through the renal artery, the amount of released nitric oxide sufficient to cause vasodilation of the renal artery bed. Embodiments of the invention are directed to apparatuses and methods that provide for both production of current densities sufficient to ablate renal nerves and terminate renal sympathetic nerve activity, and production of current densities sufficient to induce endothelium dependent vasodilation of the renal artery bed. The apparatus used for renal ablation may also be used to control renal function locally after renal denervation in accordance with embodiments of the invention.

Embodiments of the invention are directed to apparatuses and methods that stimulate and control local vascular tone via temperature control of renal vasculature. Embodiments of the invention are directed to apparatuses and methods that provide for excitation of renal nerves with a temperature gradient, such as a temperature gradient produced from the hot and cold ends of a Peltier device. Use of a Peltier device in this context advantageously provides for a low energy requirement. In accordance with some embodiments, renal nerves can be stimulated via a temperature gradient generated using infrared light delivered to the renal artery using an intra- or extravascular device.

Figure 4:
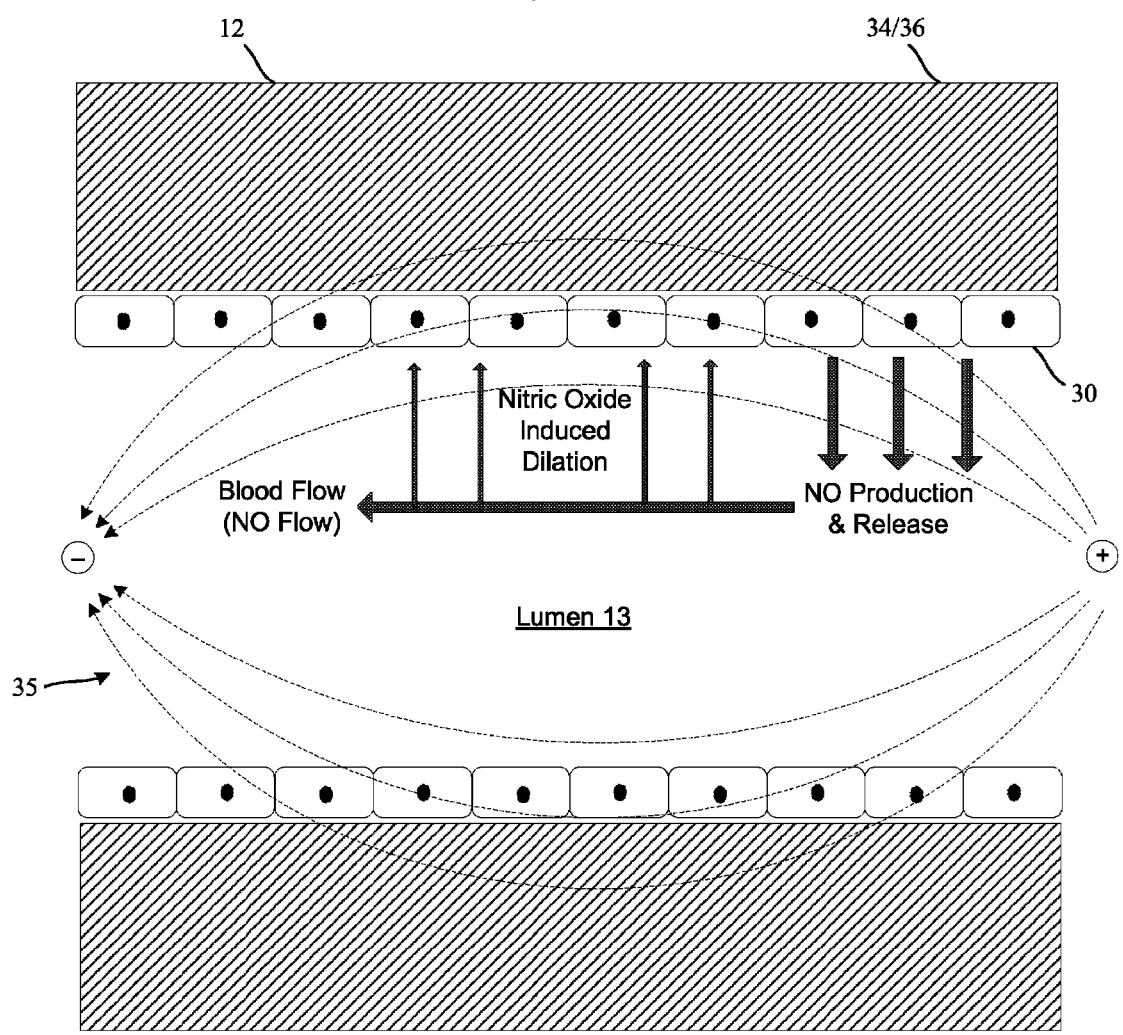
FIG. 4 illustrates a portion of a renal artery shown in cross-section including an electric field superimposed thereon, with electron flow between an anode contact and a cathode contact of an electrode arrangement in accordance with embodiments of the invention.

In FIG. 4, a portion of a patient's renal artery 12 is shown in cross-section with an electric field 35 superimposed thereon, with electron flow between an anode contact (+) and a cathode contact (−). The anode and cathode contacts represent respective contacts of an electrode arrangement configured for deployment in the lumen 13 of the renal artery 12. The electrode arrangement is controlled to stimulate and control the membrane potential on endothelium cells adjacent the electrode arrangement. For example, hyperpolarization of the internal elastic membrane of the endothelium 30 of the renal artery induces endothelium dependent vasodilation, which propagates to the distal arteriole bed directly through cell junctions and indirectly through hyperpolarization induced release of nitric oxide into the blood. Control of the electrode arrangement depicted in FIG. 4 provides for local control of renal function after renal denervation.

FIGS. 5A-6C show various embodiments of an implantable vascular apparatus 50 configured to deliver energy to innervated renal vasculature in accordance with embodiments of the invention. The embodiments shown in FIGS. 5A-6C include apparatuses 50 that provide for renal function control via renal stimulation, such as apparatuses configured to generate and control an electric field to achieve a desired membrane potential on endothelium cells of the renal artery. The embodiments shown in FIGS. 5A-6C include apparatuses for delivering thermal denervation therapy to renal vasculature, such as apparatuses that deliver thermal energy directly to the renal artery wall.

Implantable apparatuses according to the embodiments of FIGS. 5A-6C may be configured for positioning within the renal artery at one or more renal artery lumen locations, and for purposes of delivering renal denervation therapy, and subsequently implanted at a permanent renal artery lumen location to effect long-term renal function control. Apparatuses according to the embodiments of FIGS. 5A-6C may be chronically implanted at a desired renal artery lumen location for both denervation and renal function control purposes.

Figure 5A:
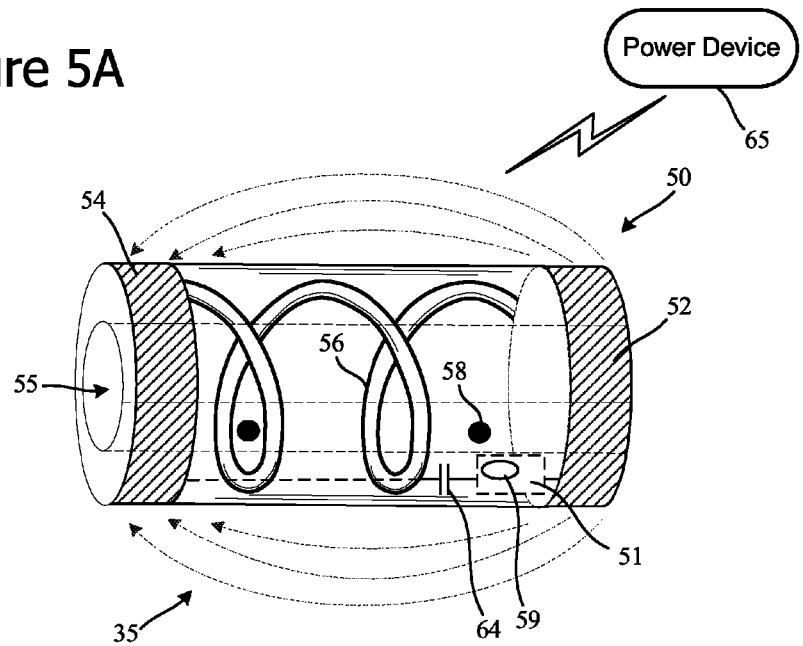
FIG. 5A illustrates an implantable vascular apparatus configured to deliver thermal energy to innervated renal vasculature in accordance with embodiments of the invention.

FIG. 5A illustrates an implantable vascular apparatus 50 configured to deliver thermal energy to innervated renal vasculature in accordance with embodiments of the invention. The implantable vascular apparatus 50 shown in FIG. 5A includes an energy source 56 and a multiplicity of electrodes 52, 54, and is dimensioned for deployment in a renal artery 12 of a patient. The implantable vascular apparatus 50 typically has a generally cylindrical shape with an inner void 55 that provides for renal arterial blood flow therethrough. The electrodes 52, 54 are preferably thermally insulated to prevent or reduce cooling of the electrodes 52, 54 by blood passing through the renal artery.

The energy source 56 for the implantable vascular apparatus 50 is coupled to the electrodes 52, 54. In the embodiment shown in FIG. 5A, the energy source 56 includes an inductive coil or antenna that receives energy from a power device 65 external of the renal artery 12. A capacitor 64 is shown connected in parallel with the coil 65, which can represent a physical component or the self-capacitance of the inductive coil 65. The power device 65 induces an AC current in the coil 56, causing heating at each of the electrodes 52, 54. Ohmic heat is produced by the induced AC current as it passes through resistive tissues of the renal artery wall to renal nerves and ganglia.

The capacitance of the capacitor 64 is preferably selected to tune the inductive coil circuit 56 to the frequency of the power device 65. The external power device 65 may be an RF energy source located outside of the body or within the body, such as within a vessel (e.g., renal vein 42 or the inferior vena cava 40), a body cavity or a subcutaneous pocket. In some embodiments, an electrical lead may be coupled to the implantable vascular apparatus 50 directly. Preferred embodiments include those that employ a separate energy source (in vivo or ex vivo) that wirelessly provides power for the implantable vascular apparatus 50.

Figure 5B:
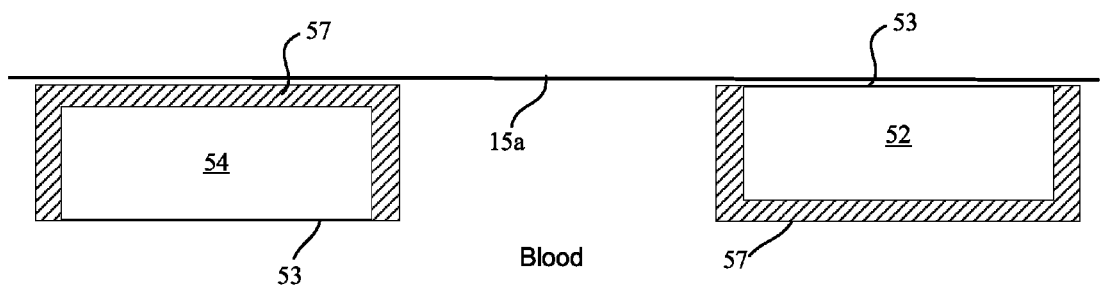
FIG. 5B shows a partial cross-section of an anode contact and a cathode contact of an electrode arrangement situated adjacent an inner wall of the renal artery or other innervated vessel that contributes to renal sympathetic nerve activity or renal function in accordance with embodiments of the invention.

FIG. 5B illustrates an electrode arrangement of an implantable vascular apparatus 50 configured for hyperpolarizing innervated renal vasculature in accordance with embodiments of the invention. The electrode arrangement shown of FIG. 5B may alternatively or additionally be used to deliver direct thermal energy to the renal artery wall via an anode of the electrode arrangement. In this configuration, it is desirable to thermally insulate the back of the anode to prevent or reduce blood cooling, and to electrically insulate the anode from the blood that flows through the vessel. The electrode arrangement shown in FIG. 5B is preferably coupled to an inductive coil or antenna, and may be implemented in an intravascular apparatus of the type generally shown in FIG. 5A or FIG. 6A, for example.

Figure 16:
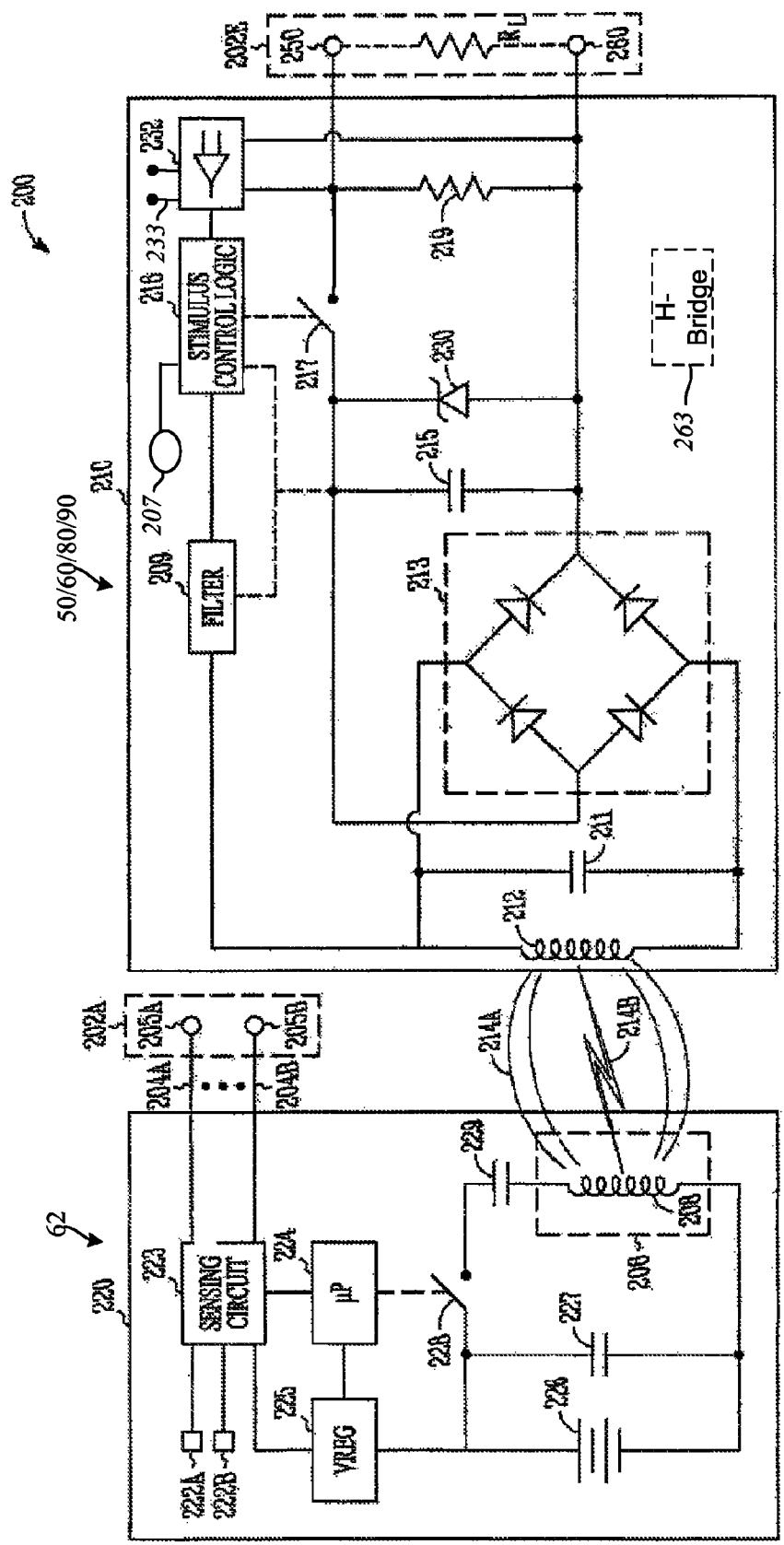
FIG. 16 is a schematic of a renal denervation and/or renal stimulation system in accordance with embodiments of the invention.

In a DC configuration, the electrode arrangement shown in FIG. 5B is coupled to a diode or rectifier that converts AC current induced in the coil or antenna 56 by an RF power device 65 to DC (see, e.g., FIG. 16). In some embodiments, a switch arrangement may be included to facilitate switching of components (e.g., capacitors, diodes, rectifiers) to selectively change the electrode arrangement configuration of the implantable vascular apparatus 50 between AC and DC configurations. Selectively changing electrode arrangement configurations of the implantable vascular apparatus 50 allows for selective delivery of thermal ablation and renal function stimulation (e.g., hyperpolarization) therapies.

FIG. 5B show partial cross-sections of anode contact 52 and cathode contact 54 of the electrode arrangement of FIG. 5A situated adjacent an inner wall 15a of the renal artery or other innervated vessel that contributes to renal sympathetic nerve activity or renal function. In FIG. 5B, the anode contact 52 is shown to include a first region 53 in contact with inner vessel wall tissue 15a and a second region 57 that extends into the lumen 13 of the vessel and is exposed to blood within the vessel. The first electrode region 53 is configured to directly contact the inner vessel wall tissue 15a, and the second electrode region 57 includes insulation that electrically insulates the second electrode region 57 from blood that flows within the vessel. The first electrode region 53 of the anode contact 52 hyperpolarizes the adjacent endothelium 30 and smooth muscle 34 of the vessel wall tissue. It is considered important that the anode contact 52 be insulated from blood flow partly as a means to prevent electro-coagulation of blood at the anode contact 52 of the implantable vascular apparatus 50.

FIG. 5B also shows a cathode contact 54 that includes a first region 53 that extends into the lumen 13 of the vessel and is exposed to blood within the vessel. The first region 53 is configured to electrically couple with the blood within the vessel. The cathode contact 54 includes a second region 57 that includes insulation for electrically insulating the cathode contact 54 from the inner vessel wall tissue 15a. In some configurations, the cathode contact 54 extends into the void 55 of the implantable vascular apparatus 50 and this extension of the cathode contact 54 is free of insulation and exposed to the blood within the vessel. The remaining portion of the cathode contact 54 is either situated out of contact with the inner vessel wall tissue 15a or includes insulation to electrically isolate the cathode contact 54 from the inner vessel wall tissue 15a.

Figure 6A:
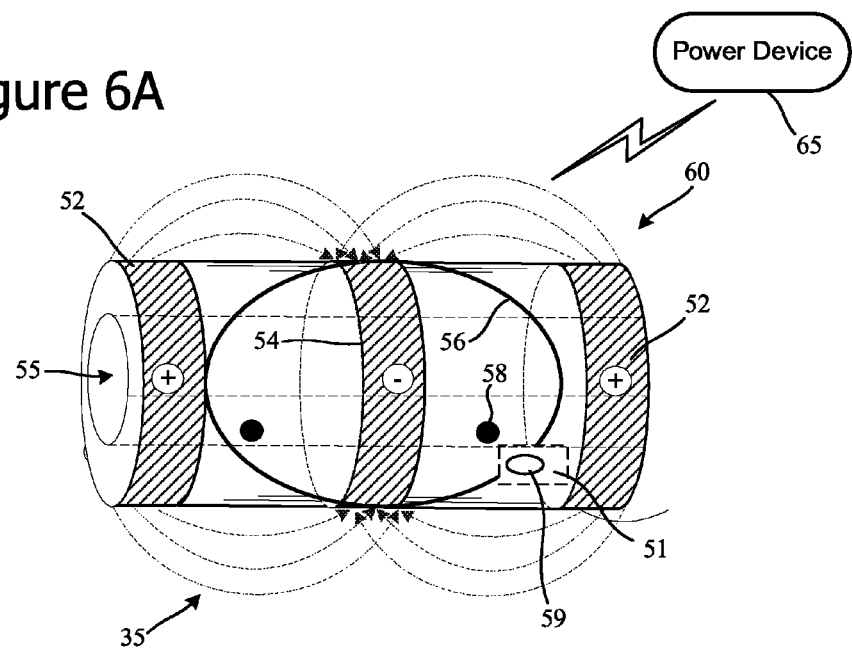
FIG. 6A illustrates an implantable vascular apparatus which includes a multiplicity of anode contacts and a common or shared cathode in accordance with embodiments of the invention.
Figure 6B:
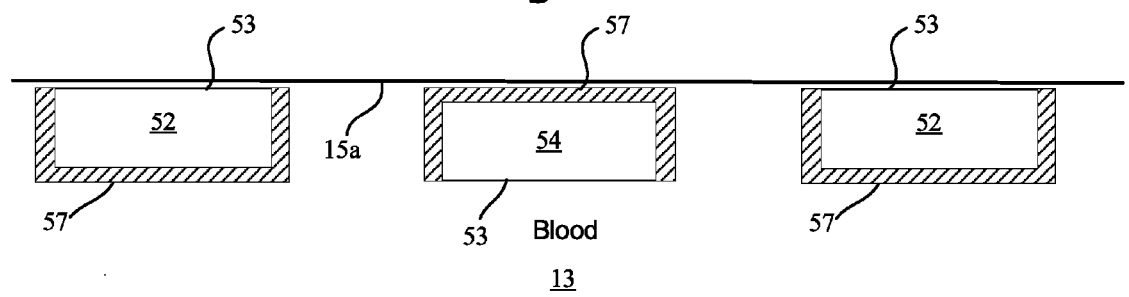
FIG. 6B shows a partial cross-section of the electrode arrangement of FIG. 6A, including two anode contacts and a shared cathode contact in accordance with embodiments of the invention.
Figure 6C:
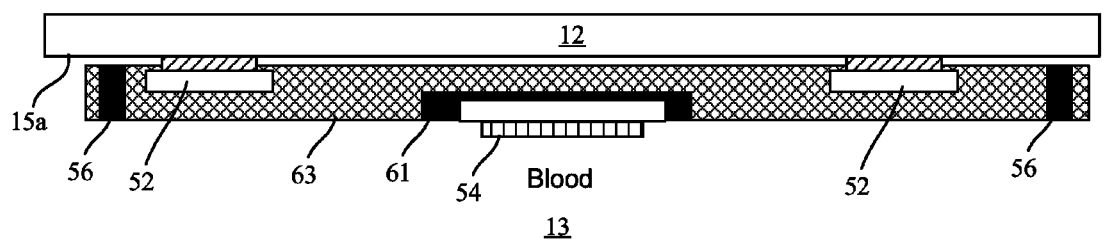
FIG. 6C shows a partial cross-section of two anode contacts and a shared cathode contact of the implantable vascular apparatus of FIG. 6A in accordance with embodiments of the invention.

FIG. 6A illustrates an implantable vascular apparatus 60 in accordance with embodiments of the invention deployed in a renal artery 12 of a patient. The implantable vascular apparatus 60 shown in FIG. 6A includes an energy source 56 and a multiplicity of electrodes 52, 54, and is dimensioned for deployment in a renal artery 12 of a patient. Additional details of the electrodes 52, 54 of the implantable vascular apparatus 60 of FIG. 6A are shown in FIGS. 6B and 6C. The implantable vascular apparatus 60 typically has a generally cylindrical shape with an inner void 55 that provides for renal arterial blood flow therethrough. The implantable vascular apparatus 60 shown in FIG. 6A includes two anode contacts 52 and a single shared cathode contact 54. The two anode contacts 52 are positioned relative to opposing ends of the implantable vascular apparatus 60, respectively, and the cathode contact 54 is positioned at a center location of the implantable vascular apparatus 60.

The energy source 56 for the implantable vascular apparatus 60 is coupled to the anode contacts 52 and the cathode contact 54, and includes an antenna configured to receive energy transmitted from a power device 65 external of the renal artery 12. The antenna 56 may comprise a coil antenna, for example. The external power device 65 may be an RF energy source located outside of the body. Preferably, the external power device 65 is an implantable device that can be positioned within the body, such as within the renal vein 42, the inferior vena cava 40, or a body cavity or subcutaneous pocket.

In some embodiments, the implantable power device 65 is positioned in proximity to the implantable vascular apparatus 60 situated within the renal artery 12 and configured to receive energy from an ex vivo power source, such as an RF generator located in proximity to the patient. The implantable power device 65 may then wirelessly transmit energy to the antenna 56 of the implantable vascular apparatus 60 located within the lumen of the renal artery 12.

In other embodiments, the implantable power device 65 receives energy from an in vivo power source via an implantable electrical lead. The in vivo power source may be a battery of an implantable medical device, such as an implantable stimulator, a cardiac rhythm management device such as a pacemaker, cardiac resynchronizer, implantable cardioverter-defibrillator, or a neurostimulation device. The implantable power device 65 may then wirelessly transmit power to the antenna or coil 56 of the implantable vascular apparatus 60 located within the lumen of the renal artery 12.

FIG. 6B show partial cross-sections of two anode contacts 52 and a cathode contact 54 of the electrode arrangement of FIG. 6A situated adjacent an inner wall 15a of the renal artery or other innervated vessel that contributes to renal sympathetic nerve activity or renal function. The anode contacts 52 and cathode contact 54 shown in FIG. 6B have the same configuration as those illustrated in FIG. 5B discussed hereinabove.

FIG. 6C show partial cross-sections of two anode contacts 52 and a cathode contact 54 of the implantable vascular apparatus 60 of FIG. 6A situated adjacent an inner wall 15a of the renal artery 12 or other innervated vessel that contributes to renal sympathetic nerve activity or renal function in accordance with embodiments of the invention. In the embodiment shown in FIG. 6C, the implantable vascular apparatus 60 comprises a stent 63 which supports the anode contacts 52 and the cathode contact 54. The two anode contacts 52 are situated on the stent 63 so as to directly contact the inner wall 15a of the renal artery 12. The anode contacts 52 may be electrically tied together and coupled to the antenna 56, or may be individually coupled to the antenna 56. It is noted that the stent 63 may support one, two or more antennae 56, and that the antennae 56 may comprise separate elements mounted on the stent 63 or be integral to the stent structure, such as one, two, or more struts of the stent 63. The cathode contact 54 is exposed to the lumen 13 of the renal artery 12 and electrically couples with blood flowing within the artery 12. An insulator 61 is disposed between the cathode contact 54 and the stent body 63 such that the cathode contact 54 is electrically isolated from the inner vessel wall 15a.

The implantable vascular apparatus 50, 60 shown in FIGS. 5A-6C may be operated in one or multiple configurations or modes. According to various embodiments, the implantable vascular apparatus 50, 60 is chronically implanted within the renal artery 12 and operable in a denervation mode. In a denervation mode of operation, the energy source 56 is controlled via an external energy device and/or an electronics module 51 coupled to the energy source 56 to generate ablative energy sufficient to denervate renal nerves and ganglia, such as by inducing electrical currents that heat the renal artery wall to a sufficiently high temperature to kill renal nerves and ganglia (e.g., necrotic coagulation of the innervated renal tissue).

For example, target renal artery tissue can be heated using the implantable vascular apparatus 50, 60, and, if the artery wall tissue temperature exceeds 50° C., the tissue can be killed. However, the target tissue will not be physically and permanently disrupted until the temperature of the target tissue exceeds about 65° C., where the collagen reforms. When the temperature within the target tissue reaches a sufficient level (e.g., >65° C.), the target tissue is thermally coagulated.

In some embodiments, the implantable vascular apparatus 50, 60 is chronically implanted within the renal artery 12 and configured to provide for renal function control via renal stimulation. An electric field 35 is generated across the anode and cathode contact 52, 54 and controlled to achieve a desired membrane potential on endothelium cells 30 adjacent the implantable vascular apparatus 50, 60. The implantable vascular apparatus 50, 60 can be controlled via the external energy device and/or an electronics module 51 coupled to the energy source 56 to control hyperpolarization of the internal elastic membrane of the endothelium 30 and the degree of endothelium dependent vasodilation. According to various embodiments, the implantable vascular apparatus 50, 60 illustrated in FIGS. 5A-6C provides for local control of renal function, which is desirable for patient's who have undergone renal denervation.

In accordance with further embodiments, the implantable vascular apparatus 50, 60 is chronically deployed within the renal artery 12 and configured to deliver renal denervation therapy in a first mode of operation, and used in a second mode of operation to provide renal stimulation therapy for renal function control following renal denervation. The implantable vascular apparatus 50, 60 may be positioned within the renal artery at one or more renal artery lumen locations for purposes of delivering renal denervation therapy to the patient's renal artery 12, and subsequently implanted at a permanent renal artery lumen location. In some embodiments, it may be desirable to chronically implant the implantable vascular apparatus 50, 60 for both denervation and renal function control purposes.

It is desirable to concentrate denervation energy in the tissues of the adventitia 36 and the vaso vasorum that include renal nerves and ganglia, and to reduce the concentration of denervation energy in the tissues of the endothelium 30 and media 34. For example, it is desirable that the renal artery inner wall tissue temperature not exceed 50° C., while the tissues of the adventitia 36 and the vaso vasorum that include renal nerves and ganglia exceed 50° C., preferably exceeding 65° C. or higher. Cooling of the endothelium 30 and tissue of the media 34 near the endothelium 30 can be achieved using a variety of apparatuses and techniques.

For example, cooling of the endothelium 30 and tissue of the media 34 near the endothelium 30 can be achieved by channeling blood flow in the renal artery to locations adjacent the endothelium 30. Local endothelium/medial tissue cooling may be provided using various devices, such as thermoelectric elements (e.g., Peltier devices) or a separate cooling catheter, cooling balloon, cryocatheter or cryoballoon arrangement. For example, a separate cooling arrangement comprising a balloon or cryoballoon can be navigated to the renal artery 12, and positioned within the void 55 of the implantable vascular apparatus 50, 60. The balloon can be inflated with the cooling arrangement positioned within the void 55 to provide local cooling to the endothelium 30 and medial tissue. It is noted that in electrode arrangement embodiments that employ direct heating elements, these elements can be thermally insulated relative to the cooling arrangement so as to maintain efficient thermal transfer of heat between the direct heating elements to the vessel wall.

In some embodiments according to FIGS. 5A-6C, power rectification, conditioning, and/or control electronics is included as part of a power device 65 external to the renal artery 12, and the energy received and delivered by the energy source 56 of the implantable vascular apparatus 50, 60 is entirely or at least mostly controlled by the external power device electronics 65. In other embodiments, at least some of the power rectification, conditioning, and control electronics needed to controllably deliver denervation and renal stimulation energy to renal artery tissue are included as part of an electronics module 51 of the implantable vascular apparatus 50, 60.

For example, and in accordance with various embodiments, a tank circuit of the electronics module 51 or other circuitry may be coupled to the energy source 56 of the implantable vascular apparatus 50, 60 to facilitate rectification and conditioning of received energy and controlled delivery of energy to renal artery tissue. The tank circuit may include a storage capacitor that is charged to a predetermined voltage in response to energy received by the inductive coil 56. The tank circuit or other section of the electronics module 51 may include logic circuitry or a microprocessor that controls voltage and current delivery parameters for one or both of denervation and renal stimulation modes of operation. Control signals for regulating energy reception and delivery parameters may be impressed in the energy source signal generated by the external power device 65 (e.g., an RF signal for wireless energy transfer or an electrical signal for wireline energy transfer), preferably in an encoded format if wirelessly transmitted. It is noted that the tank circuit may alternatively be incorporated in the external power 65 device, and the coil 56 of the implantable vascular apparatus 50, 60 may be configured as an antenna that receives energy from the external power device 65.

The electronics module 51 may include or be coupled to one or more temperature sensors 59 which sense temperature at the implantable vascular apparatus 50, 60 and/or the inner vessel wall of the renal artery 12. Temperature data acquired by the temperature sensor 59 is preferably communicated to the electronics module 51 via a conductor. The electronics module 51 transmits a signal that incorporates the temperature data to a device external of the renal artery 12 via the coil 56 or a separate antenna, preferably in an encoded format. The temperature data is useful for controlling the operation of the implantable vascular apparatus 50, 60, such as by controlling the magnitude and duration of current/heat generation for one or both of renal denervation and renal stimulation procedures. As was discussed previously, the operation of the implantable vascular apparatus 50, 60 can be controlled by the electronics module 51, a device external of the implantable vascular apparatus 50, 60 (e.g., power device 65 or a patient-external device), or a combination of control resources.

Figure 7:
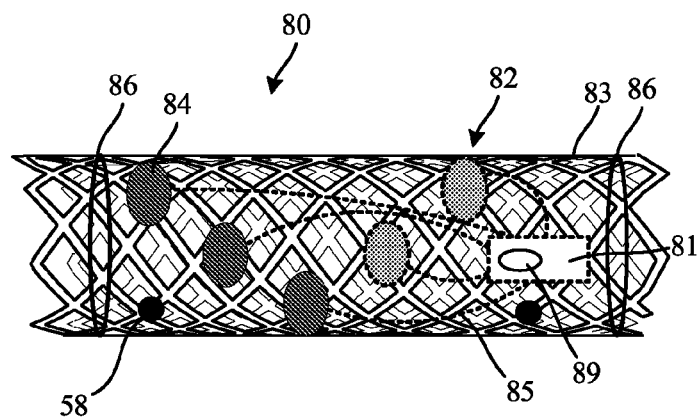
FIGS. 7-9 illustrate embodiments of an implantable intravascular apparatus comprising one or more thermoelectric elements configured to deliver denervation therapy and/or renal stimulation therapy to innervated renal vasculature in accordance with embodiments of the invention.
Figure 8:
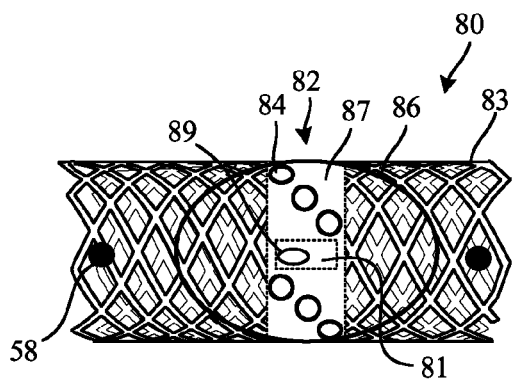
Figure 9:
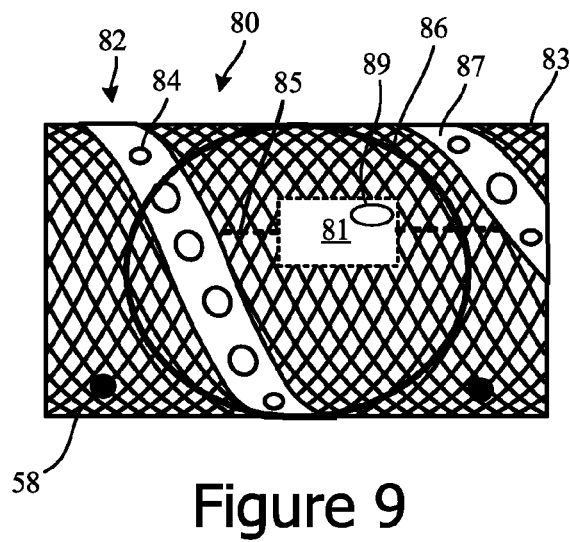

FIGS. 7-9 illustrate embodiments of an implantable vascular apparatus 80 configured to deliver denervation therapy and/or renal stimulation therapy to renal vasculature. The embodiments shown in FIGS. 7-9 includes a support structure 83 dimensioned for deployment at the renal artery 12. The support structure 83 is preferably configured for chronic fixation within the lumen of the renal artery 12, and may be implemented as a stent. A thermal transfer arrangement 82 is supported by the support structure 83 and comprises one or more thermoelectric elements 84 configured to thermally couple to the inner wall of the renal artery 12. The thermoelectric elements 84 preferably comprise solid-state thermoelectric elements, such as Peltier elements. Various Peltier-effect elements and support, connection, and control arrangements and methodologies that can be adapted for use in embodiments of the present invention are disclosed in commonly owned U.S. Pat. No. 7,238,184, which is incorporated herein by reference.

In FIGS. 7-9, the thermal transfer arrangement 82 comprises a number of thermoelectric elements 84 distributed on the surface of the support structure 83 in accordance with a predetermined pattern. In FIG. 7, a number of thermoelectric elements 84 are situated in relative isolation to one another on the surface of the support structure 83 in accordance with a generally spiral or helical pattern.

In FIG. 8, a number of thermoelectric elements 84 are situated on a substrate 87, which is shown to have a generally cylindrical shape that encircles the support structure 83. A number of thermoelectric elements 84 are situated on the substrate 87 in accordance with a generally spiral or helical pattern. The substrate 87 may be formed from a thermally conductive material, a thermally insulating material, or a combination of strategically positioned thermally conductive and thermally insulating material.

In FIG. 9, a number of thermoelectric elements 84 are situated on a substrate 87, which is shown to have a generally spiral that encompasses at least one revolution of the support structure 83. It is noted that some embodiments may employ two or more substrates 87 having a spiral shape that partially or completely encompasses at least one revolution of the support structure 83. The thermoelectric elements 84 of these two or more substrates 87 may be thermally coupled or decoupled from one another by appropriate positioning of thermally conducting and/or insulating material.

In FIGS. 8 and 9, selected ones or sets of the thermoelectric elements 84 may be disposed on thermally conductive and/or thermally insulating portions of the substrate 87. For example, several thermoelectric elements 84 may be disposed on thermally conductive portions of the substrate 87 to provide for increased thermal energy output and/or an increased surface area for generating thermal energy. Selected ones or sets of the thermoelectric elements 84 may be disposed on thermally insulating portions of the substrate 87, allowing for controlled heating and cooling of selected portions of the thermal transfer arrangement 82.

Figure 10:
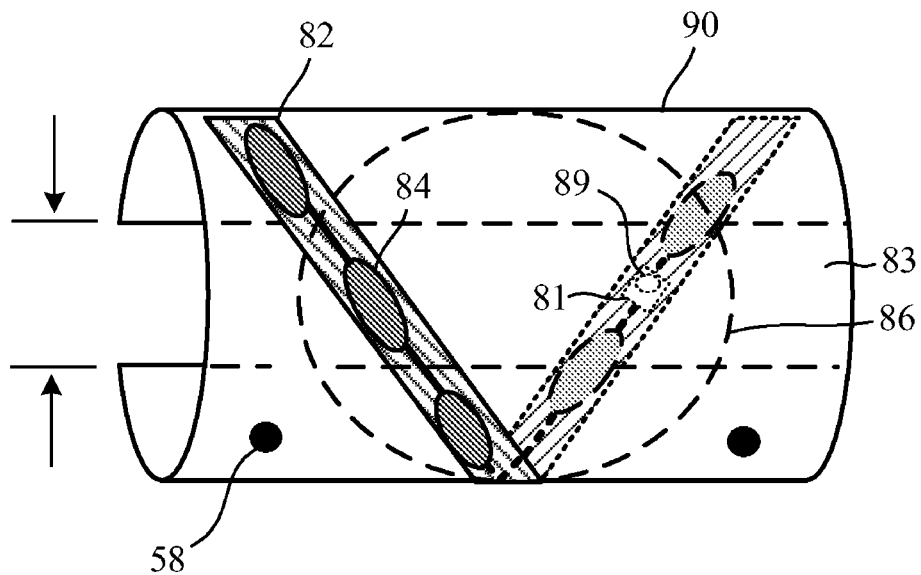
FIGS. 10 and 11 illustrate embodiments of an implantable extravascular apparatus comprising one or more thermoelectric elements configured to deliver denervation therapy and/or renal stimulation therapy to innervated renal vasculature in accordance with embodiments of the invention.
Figure 11:
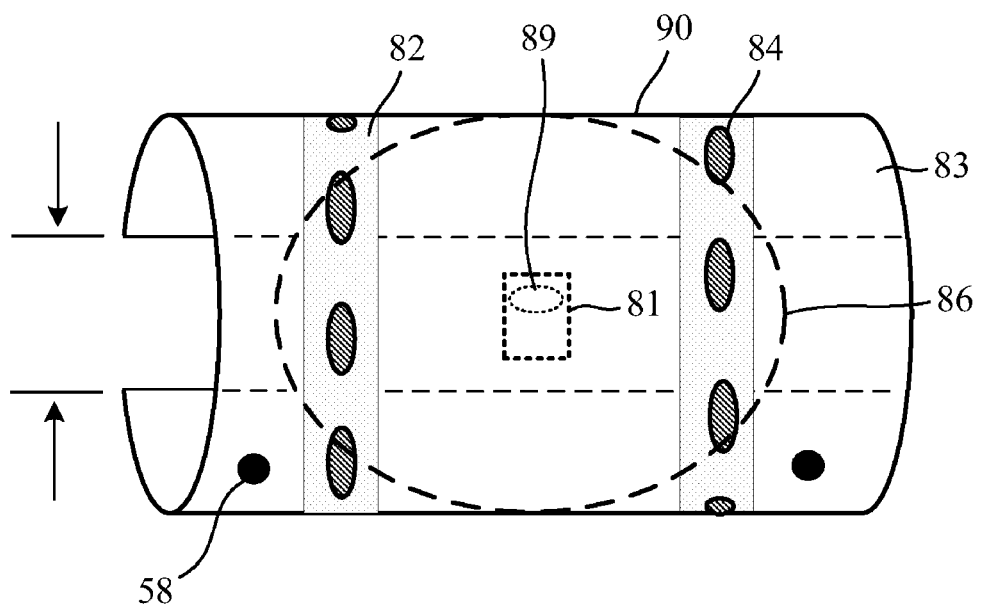

FIGS. 10 and 11 illustrate extravascular embodiments of a wireless implantable vascular apparatus 90 configured to deliver renal denervation therapy and/or stimulation therapy to control renal function. The embodiments shown in FIGS. 10 and 11 include a support structure 83 configured for deployment on an outer wall of the renal artery 12. The support structure 83 is preferably configured for chronic placement at the outer wall of the renal artery 12, and may be implemented as a cuff or clamp arrangement. A percutaneous intrathoracic access procedure, such as a laparoscopic, thoracoscopic, or other minimally invasive surgical procedure, is preferably used to place the wireless implantable vascular apparatus 90 on the outer wall of the renal artery 12.

The wireless implantable vascular apparatus 90 shown in FIGS. 10 and 11 comprise a thermal transfer arrangement 82 supported by the support structure 83 and includes one or more thermoelectric elements 84 configured to thermally couple to the outer wall of the renal artery 12. The thermoelectric elements 84 preferably comprise solid-state thermoelectric elements, such as Peltier elements. Although shown as comprising thermoelectric elements 84 in FIGS. 10 and 11, it is understood that the electrode arrangements of the intravascular renal artery apparatuses previously described with reference to FIGS. 5A-6C can be adapted for extravascular deployment on the support structure 83 shown in FIGS. 10 and 11.

The thermoelectric elements 84 are shown distributed on the surface of the support structure 83 in accordance with a predetermined pattern. In FIG. 10, a number of thermoelectric elements 84 are situated on the surface of the support structure 83 in accordance with a generally spiral or helical pattern. In FIG. 11, a number of thermoelectric elements 84 are situated on a substrate 87 that has a generally cylindrical shape that encircles the support structure 83. Two substrates 87 are shown for illustrative purposes in FIG. 11 with the thermoelectric elements 84 of the two substrates 87 arranged in a staggered configuration, such that at least a full revolution of renal artery wall tissue is subjected to treatment. It is understood that one or more than two substrates 87 may be employed. In some embodiments, some or all of the thermoelectric elements 84 may be thermally non-interactive with other thermoelectric elements 84 on the support structure 83. In other embodiments, some or all of the thermoelectric elements 84 may be thermally interactive with other thermoelectric elements 84 on the support structure 83.

The support structure 83 may incorporate a cuff mechanism that can be manipulated so that opposing edges of the cuff contact each other. Known cuff coupling mechanism may be used, such as a circumferential or annular cuff implementation. The support structure 83 may include other coupling mechanisms, such as a spiral or helical shaped coupling mechanism, among other configurations. The coupling mechanism may be integral to the support structure 83, such as by incorporation of an interlocking arrangement disposed along all or a portion of the opposing edges of the support structure 83 (e.g., a latching arrangement). A spiral or helical coupling mechanism may provide for in situ coupling of the support structure 83 to the outer wall of the renal artery 12, such as by wrapping a spiral or helical shape memory portion of the support structure 83 around the renal artery 12. Cuff embodiments in accordance with the present invention may be implemented to include features of various known vascular and nerve cuff structures, such as those disclosed in U.S. Pat. Nos. 7,584,004; 6,106,477; 5,251,634; and 4,649,936; and in U.S. Patent Publication No. 2008/0004673, which are incorporated herein by reference.

In FIGS. 7-11, each of the thermoelectric elements 84 is coupled to an electronics module 81 via a respective conductor 85. The electronics module 81 is supported by the support structure 83 and coupled to the thermal transfer arrangement 82 and an antenna arrangement 86, which is also supported by the support structure 83. The electronics module 81 preferably includes power circuitry configured to receive energy from a power source external of the wireless implantable apparatus, and preferably external of the renal artery 12, wirelessly via the antenna arrangement 86. The antenna arrangement 86 may include one or more antennae of varying configuration.

The antenna arrangement 86 shown in FIG. 7, for example, includes two loop antennae having a generally concentric shape that is supported by the support structure 83. The antenna arrangement 86 shown in FIGS. 8 and 9, by way of further example, includes one or more loop antennae having a generally oval shape that is supported by the support structure 83. In other embodiments, one, two, or more of the support structure 83 (e.g., struts of a stent) may be configured as antennae of the antenna arrangement 86.

The external power source may be implemented as power device 65 shown in FIGS. 5 and 6 or other power device described herein. For example, the power source may comprise a patient-external power source (e.g., a programmer, PC, portable communicator), an implantable power source (implantable medical device equipped with a battery or passive energy collector such as an inductive coil or other energy harvester), or both a patient-external power source and an implantable power source that operate cooperatively to supply energy to the wireless implantable vascular apparatus 80, 90.

In some embodiments, the thermoelectric elements 84 are configured or controlled to operate in a hyperthermic mode, and deliver thermal denervation therapy to the renal artery. In other embodiments, the thermoelectric elements 84 are configured or controlled to selectively operate in a hyperthermic mode, for thermally denervating the renal artery, and a hypothermic mode, for cooling endothelial and medial layer tissue. For example, the thermoelectric elements 84 may be configured or controlled to selectively operate in a hyperthermic mode and a hypothermic mode in a sequential manner or concurrently.

The electronics module 81 may incorporate a control circuit coupled to the power circuitry. The control circuit may include logic circuitry or a microprocessor configured to coordinate delivery of hypothermic ablation therapy to freeze renal nerves and terminate renal sympathetic nerve activity in a hypothermic mode of operation. The control circuit may be configured to coordinate delivery of hyperthermic therapy to at least heat renal nerves to above freezing, such as for delivering a sequence of freeze/thaw therapy cycles or a sequence of freeze/thaw/heat therapy cycles.

The control circuit may be configured to coordinate delivery of a hyperthermic ablation therapy to ablate renal nerves and terminate renal sympathetic nerve activity in a hyperthermic mode of operation. During a hyperthermic mode of operation, at least some elements or portion of the thermal transfer arrangement 82 may be operated in a hypothermic mode to provide cooling to the endothelium and media of the renal artery. The electronics module 81 may include or be coupled to one or more temperature sensors 89 which sense temperature at the thermal transfer arrangement 82 and/or the inner vessel wall of the renal artery 12.

As was previously described, temperature data acquired by the temperature sensor 89 is preferably communicated to the electronics module 81, via the antenna arrangement 86 or a separate antenna. The electronics module 81 transmits a signal that incorporates the temperature data to a device external of the renal artery 12, preferably in an encoded format. The temperature data is useful for controlling the operation of the implantable vascular apparatus 80, 90, such as by controlling the magnitude and duration of heat generation for one or both of renal denervation and renal stimulation procedures.

In some configurations, a first set of thermoelectric elements 84 is configured or controlled to operate in a hyperthermic mode, while another set of thermoelectric elements 84 is configured or controlled to operate in a hypothermic mode. In other configurations, all or a subset of the thermoelectric elements 84 are controlled to operate in a hyperthermic mode during a first duration of time, and then switch to operate in a hypothermic mode during a second duration of time. For example, the thermoelectric elements 84 can be driven to freeze renal nerves and ganglia in a hypothermic mode, and driven to generate and transfer heat to renal nerves and ganglia sufficient to kill renal nerves and ganglia in a hyperthermic mode Innervated and other renal vasculature may be subject to temperature cycling that involves transfer of thermal energy between the wireless implantable apparatus and renal tissue to achieve a desired freeze/thaw/heating profile.

Details of useful components and methodologies that can be adapted and incorporated in various embodiments of the invention are disclosed in commonly owned U.S. Pat. No. 7,238,184 and U.S. Patent Publication No. 2009/0024194, which are incorporated herein by reference. A detailed discussion of renal nerve structures and degrees of nerve disruption that can be achieved using embodiments of the invention is provided in commonly owned U.S. Provisional Application Ser. No. 61/291,476, filed Dec. 31, 2009, which is incorporated herein by reference.

One or more physiologic parameters can be monitored during the renal denervation and renal stimulation procedures to determine the effect of these procedures on the patient's renal sympathetic nerve activity or renal function. For example, and as shown in FIGS. 5-11, an electrode arrangement 58 may be situated on the implantable vascular apparatus 50/60/80/90 to contact the inner or outer wall of the renal artery 12. The electrode arrangement 58 is preferably coupled to an electronics module 51/81 of the implantable vascular apparatus 50/60/80/90. The electrode arrangement 58 may incorporate one or multiple electrodes for sensing one or more physiologic parameters using either a unipolar or multipolar sensing configuration.

In some embodiments, the electrode arrangement 58 may be configured to measure nerve impulses transmitted along renal nerve fibers of the renal artery 12, including those that couple to or pass through the renal ganglion 24. By way of further example, one or more physiological parameters that are sensitive to changes in renal sympathetic nerve activity or renal function may be monitored using the electrode arrangement 58. The efficacy of the renal ablation may be determined based on measured changes in the physiological parameter(s).

Other sensors may be used alternatively or in addition to those of the electrode arrangement 58, which may include implantable or cutaneous (e.g., patient-external) sensors. For example, an impedance sensor and/or a pressure sensor may be used to monitor lung tissue impedance and/or blood pressure. Renal artery stimulation can be delivered and controlled automatically in response to physiologic sensors, such as lung tissue impedance and/or blood pressure measured using an impedance sensor and/or a pressure sensor. For example, the electrode arrangement 58 or other physiologic sensor may be used to sense ECG signals or a surrogate signal which is modulated by cardiac activity. Stimulation pulses to renal vasculature may be synchronized with the heart rhythm and pulse as part of renal stimulation therapy to control renal function.

Useful physiologic sensors that can be used in conjunction with an implantable vascular apparatus 50/60/80/90 for monitoring patient response to renal denervation and/or stimulation therapies and for automatically adjusting these therapies include sensors that measure nerve activity, cardiac electrical and/or mechanical activity (e.g., ECG, heart sounds), blood pressure, blood flow (e.g., flow or plethysmographic sensing), blood gas saturation (oxygen, carbon dioxide, etc.) via oximetry, blood chemistry, lung sounds, and impedance. Suitable apparatuses for these purposes are disclosed in commonly owned U.S. Patent Publication No. 2008/0234780 and in U.S. Patent Publication No. 2005/0192638, which are incorporated herein by reference.

Various sensors and monitoring processes may be implemented for purposes of detecting re-innervation of the renal artery following renal denervation. Renal nerve regeneration and re-innervation of the renal artery can occur weeks or months after renal denervation therapy as long as the endoneural tubes of the renal nerve fibers are intact. A chronically implanted vascular apparatus 50/60/80/90 in accordance with embodiments of the invention can be used to monitor for re-innervation of the renal artery following renal denervation.

One approach to monitoring for re-innervation of the renal artery involves monitoring for changes in a renal nerve activity signal during hypothermic stunning of renal nerves using sub-lethal cooling. An aspect of hypothermia on nerves is that the nerves may be stunned by sub-lethal cooling, recovering full function when cooling is terminated. By monitoring a renal nerve activity signal via electrodes, for example, changes of this signal during and after hypothermic stunning of renal vasculature can be detected. If sensed electrical activity decreases during stunning, it can be assumed that living nerves are nearby, indicating that re-innervation is occurring or has occurred and that additional renal denervation therapy is needed. It is noted that this monitoring approach may also be used for assessing the efficacy of a renal denervation therapy.

In some embodiments, a controller or processor of the implantable vascular apparatus 50/60/80/90 or other implantable or patient-external control device may be configured to coordinate monitoring of at least one physiologic parameter that facilitates detection of renal sympathetic nerve activity associated with re-innervation of the renal artery. Monitoring for renal sympathetic nerve activity associated with re-innervation of the renal artery can be conducted in a monitoring mode of the implantable vascular apparatus 50/60/80/90, in which hypothermic and/or hyperthermic therapy delivery is disabled.

Automatic or semi-automatic control of the renal artery stimulation and/or renal denervation may be effected by the electronics module 51/81 of the implantable vascular apparatus 50/60/80/90, by the controller of an external device 65, by an electronics module of an implantable device communicatively linked to the implantable vascular apparatus 50/60/80/90, or by a combination of two or more of these control resources.

Various components, devices, and methodologies that can be adapted for use in the context of various embodiments of the invention are disclosed in commonly owned U.S. Publication No. 2007/0260281 and 2009/0204170, each of which is incorporated herein by reference.

FIGS. 12-15 illustrate several embodiments of an implantable vascular apparatus 50/60/80/90 that receives energy wirelessly from an implantable or patient-external energy source in accordance with the invention. Although shown as comprising intravascular vascular apparatuses in FIGS. 12-15, it is understood that the extravascular renal apparatuses previously described with reference to FIGS. 10 and 11 may be used in the context of the embodiments shown in FIGS. 12-15, and that a combination of intravascular and extravascular renal apparatuses can be employed.

Figure 12:
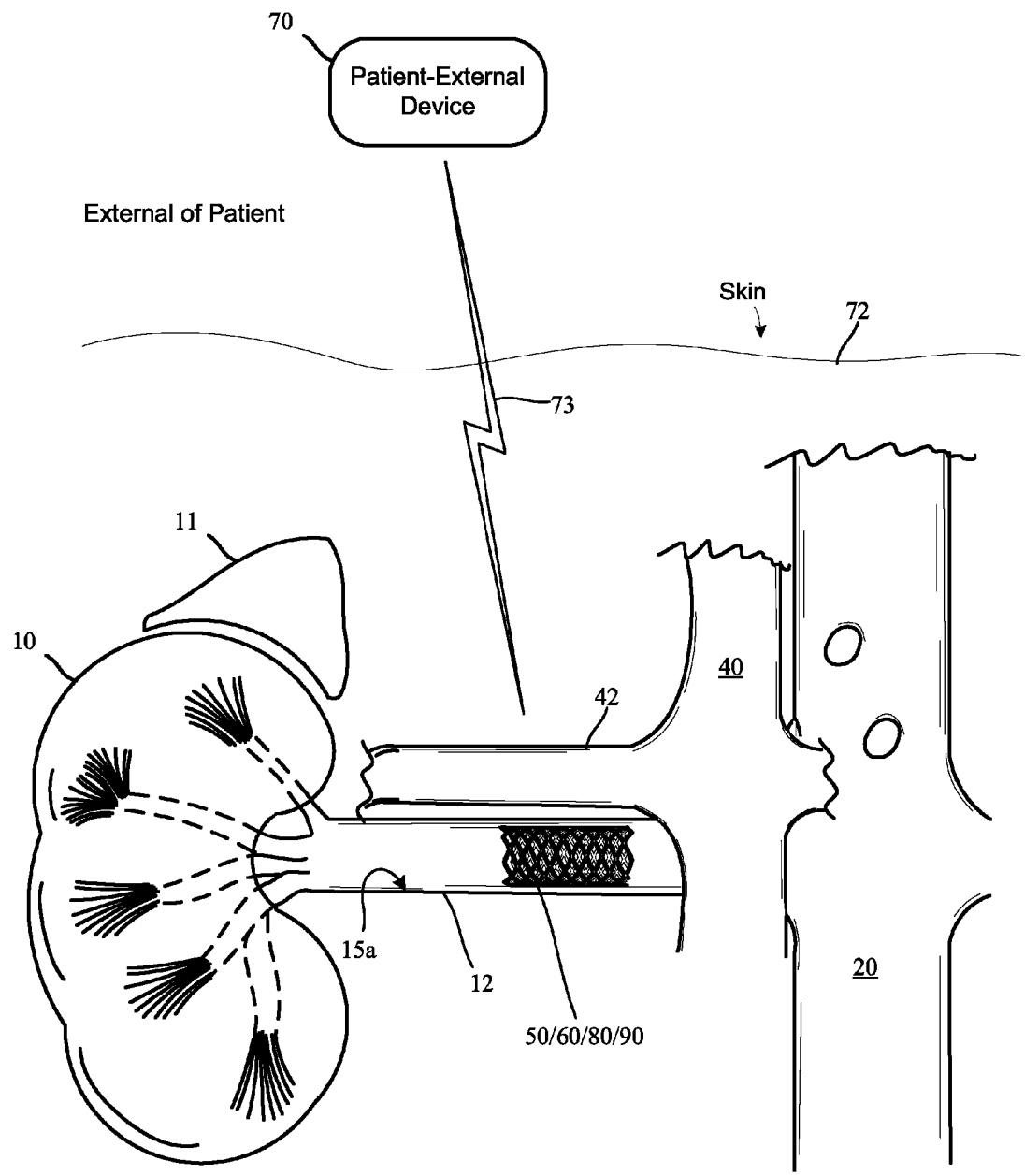
FIGS. 12-15 illustrate various embodiments of an implantable renal artery apparatus the receives energy wirelessly from an implantable or patient-external energy source for purposes of delivering one or both of renal denervation and stimulation therapy in accordance with embodiments of the invention.

FIG. 12 illustrates an embodiment that includes an implantable vascular apparatus 50/60/80/90 of a type previously described deployed chronically within a patient's renal artery 12. The implantable vascular apparatus 50/60/80/90 includes an inductive coil or an antenna that receives energy from a device 70 located external of the patient via a transcutaneous path through the skin 72.

In some embodiments, the patient-external device 70 is used to transfer energy sufficient to allow the implantable vascular apparatus 50/60/80/90 to deliver renal denervation therapy. The patient-external device 70 preferably includes an RF generator that generates an RF signal having a frequency typically in the range of 100 KHz to 10 MHz. The RF generator may be incorporated in or coupled to a processing device, such as a programmer, PC, or portable communicator.

Following renal denervation therapy, and assuming the patient is ambulatory thereafter, the patient may be provided a portable RF generator 70 in accordance with various embodiments. The portable RF generator 70 is configured to transfer energy transcutaneously to the implantable vascular apparatus 50/60/80/90. The energy transfer from the portable RF generator 70 and the implantable vascular apparatus 50/60/80/90 is sufficient to allow the implantable vascular apparatus 50/60/80/90 to deliver renal stimulation therapy to control renal function on a long-term ambulatory basis. A portable RF generator 70 may also be used in the embodiments shown in FIGS. 13-15.

The portable RF generator 70 preferably includes electronics for monitoring renal functions via one or more physiologic sensor of a type previously described, and for controlling stimulation energy to the renal artery 12. The portable RF generator 70 may also incorporate a communications interface that facilitates communications with a separate device or system, such as a programmer, medical system, PC, network server, wireless access point, cellphone, smartphone, or PDA. For example, the communications interface of the portable RF generator 70 may include one or both of a hardwire or wireless communication interface. Exemplary interfaces include USB; IEEE 1394 FireWire; Wi-Fi; cellular; Medical Implant Communication Service (MICS); Industrial, Scientific and Medical (ISM) radio band; and Short Range Devices (SRD) radio band, among others.

Figure 13:
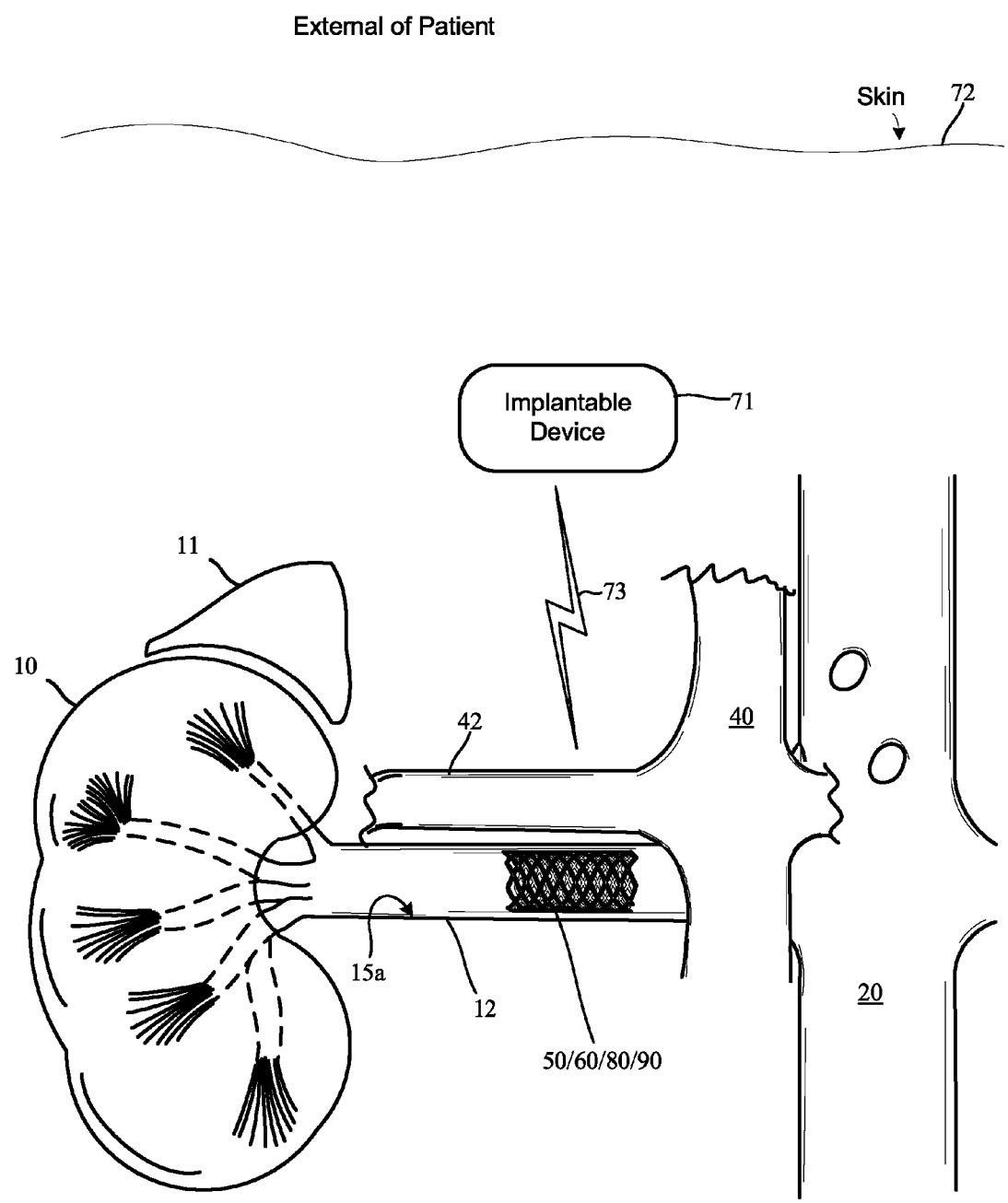

FIG. 13 illustrates an embodiment of an implantable vascular apparatus 50/60/80/90 the receives energy wirelessly from an implantable device 71. The implantable vascular apparatus 50/60/80/90 is of a type previously described and is shown deployed chronically within a patient's renal artery 12. The implantable vascular apparatus 50/60/80/90 includes an inductive coil or an antenna that receives energy from the implantable device 71, which is positioned within the patient's body below the skin 72. The implantable device 71 provides an in vivo power source for the implantable vascular apparatus 50/60/80/90. This power source may be a battery of an implantable medical device, such as an implantable stimulator, a cardiac rhythm management device such as a pacemaker, cardiac resynchronizer, or implantable cardioverter-defibrillator, a neurostimulation device, a drug pump, or other powered implantable apparatus. Alternatively, the implantable device 71 may comprise a battery and electronics that are dedicated to supplying wireless power and communications to the implantable vascular apparatus 50/60/80/90. The battery may be rechargeable from an external power transmitter.

Figure 14:
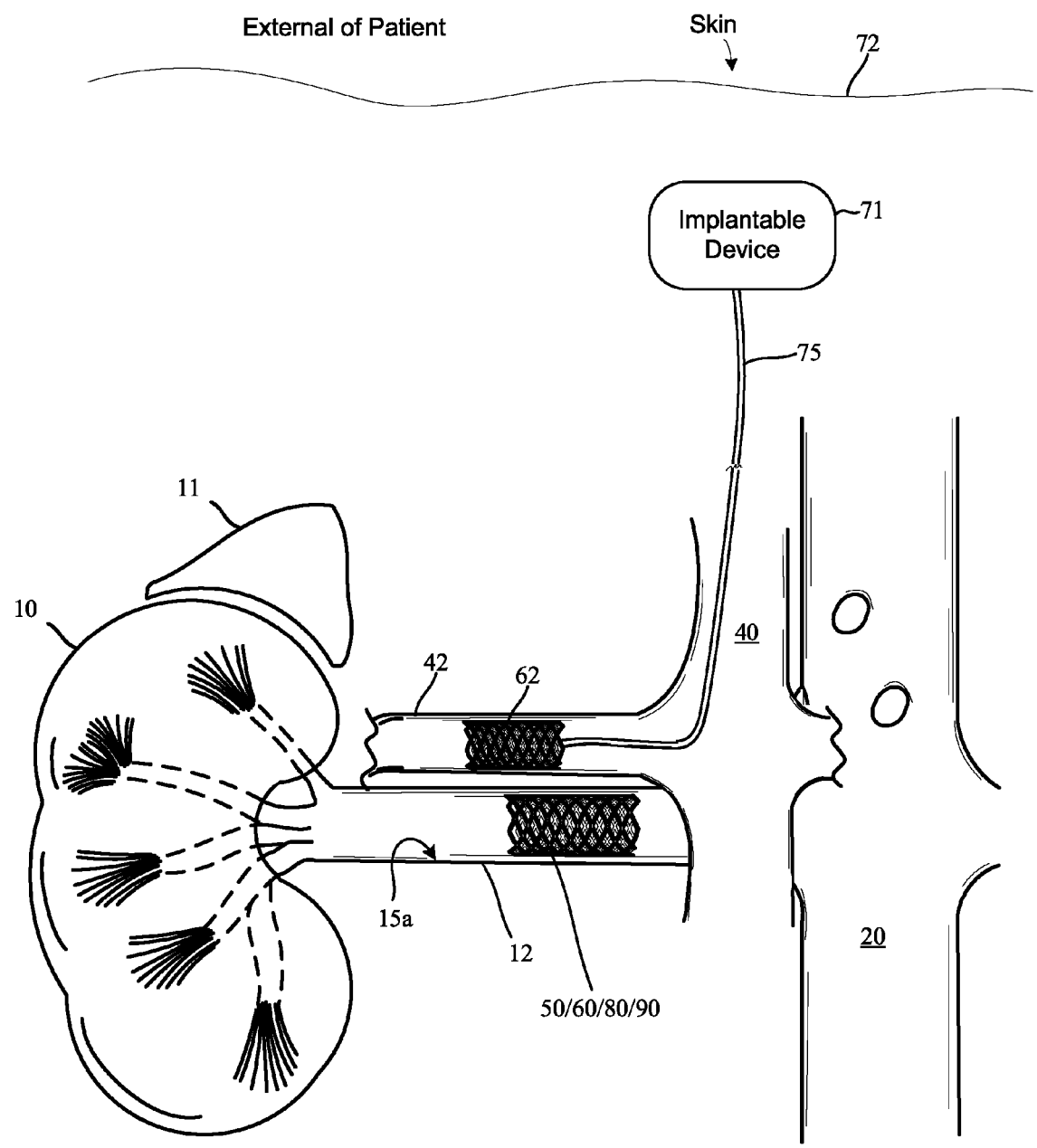
Figure 15:
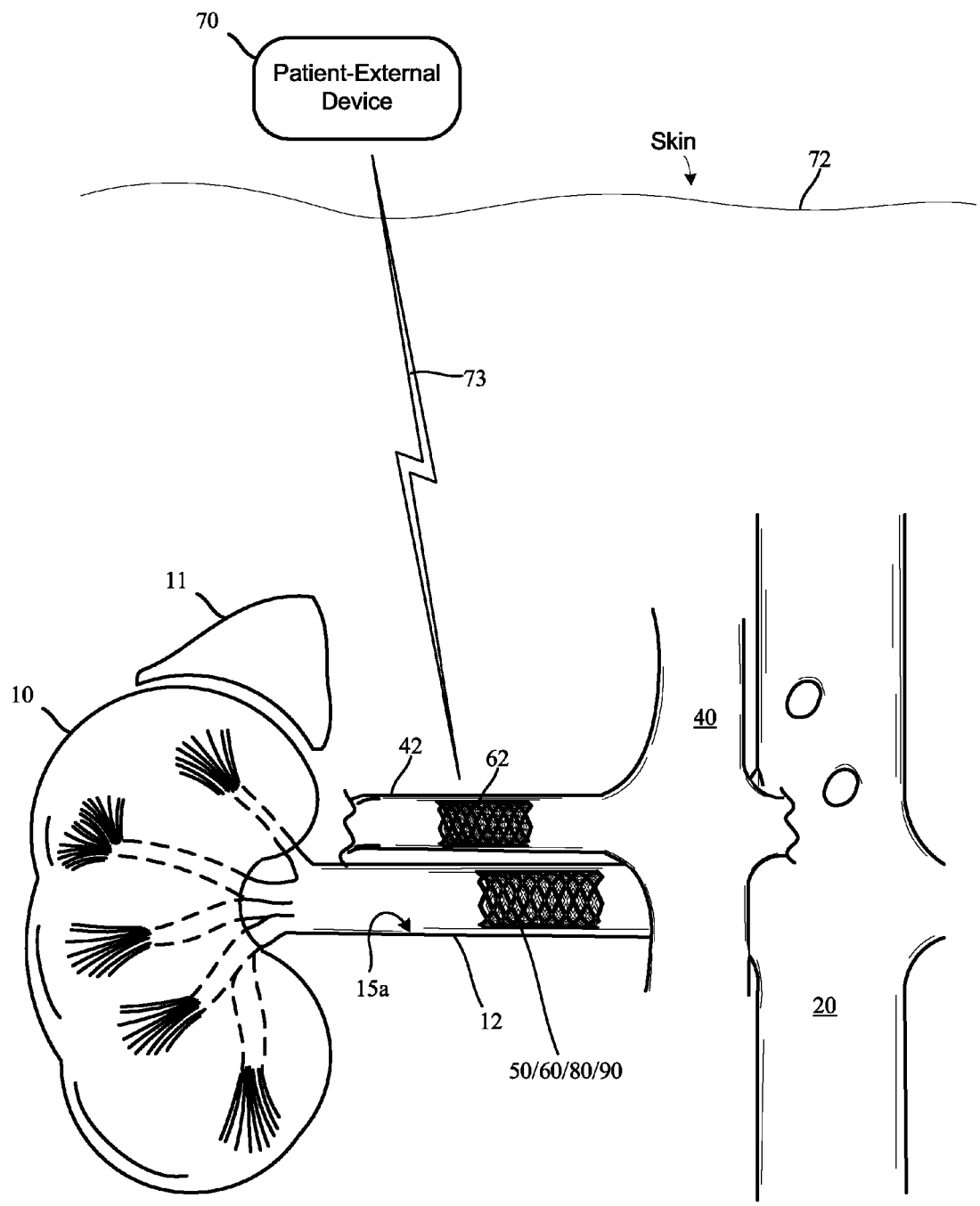

FIGS. 14 and 15 illustrate embodiments of an implantable vascular apparatus 50/60/80/90 configured to receive energy wirelessly from a separate intravascular or extravascular energy source 62 in accordance with the invention. Although vascular apparatuses 50/60/80/90 and 62 are shown as intravascular apparatuses in FIGS. 14 and 15, it is understood that the extravascular renal apparatuses previously described with reference to FIGS. 10 and 11 may be used in the context of the embodiments shown in FIGS. 14 and 15, and that a combination of intravascular and extravascular apparatuses can be employed.

In FIGS. 14 and 15, a transmit coil or antenna is provided on a source stent 62 configured for deployment in the renal vein 42. A receive stent 50/60/80/90 is configured for deployment in the adjacent renal artery 12. The source stent 62 supplies RF power using an RF transmit coil or antenna that is efficiently coupled to a receiver coil or antenna on the receive stent 50/60/80/90 via a transvenous path. In some embodiments, as is shown in FIG. 14, power is supplied to the source stent 62 from an implantable device 71, such as an implantable pulse generator, via a lead 75 that passes through the vena cava 40.

The implantable device 71 may include a pulse generator positioned in a pectoral pocket. Transmit coil current for the source stent 62 is supplied by the pulse generator via the lead 75. The pulse generator can contain multiple functions such as defibrillation and cardiac pacing. RF power is efficiently transmitted over the relatively short distance from the source stent 62 to the receive stent 50/60/80/90 in the renal artery 12. In other embodiments, as is shown in FIG. 15, power is supplied to the source stent 62 from a patient-external device 70, via a system-based or portable RF generator.

Anodes at the end of the receive stent 50/60/80/90 are configured to contact the renal artery wall 15a and to hyperpolarize the tissue and induce endothelium dependent vasodilation, as previously described. The anodes are insulated from the blood within the renal artery 12, while the cathode is positioned at the center of the receive stent 50/60/80/90 and is in contact with blood, but insulated from the renal artery wall 15a. As was previously discussed, renal artery stimulation can occur automatically in response to physiologic sensors that measure, for example, lung tissue impedance and/or blood pressure. Renal artery stimulation can be initiated manually from a remote pulse generator controller, such as a programmer or portable communicator. In addition or in the alternative, ablation of the renal nerves and ganglia can be accomplished by inducing sufficiently large currents in renal artery tissue surrounding the receive stent electrodes using the pulse generator 71 or an external controller/transmitter 70. The ablation can be controlled by a temperature measurement made on the receive stent 50/60/80/90 and transmitted to the pulse generator 71 or patient-external controller/transmitter 70.

FIG. 16 is a schematic of a renal denervation and/or renal function control system in accordance with embodiments of the invention. FIG. 16 shows circuitry 200 of two primary apparatuses that are wirelessly linked together. The components of circuitry 200 and/or functions implemented by circuitry 200 may be distributed among an implantable source apparatus 62, an implantable receive apparatus 50/60/80/90, and an external RF generator in accordance with various embodiments. For example, and in accordance with some embodiments, only circuitry of the coil 208 shown in circuitry 220 is included in the implantable source apparatus 62, while the remaining components of circuitry 220 are included in a pulse generator or other implantable medical device which is coupled to the circuitry of coil 208. It is understood that at least some of the components of circuit 220 are included or otherwise coupled to the implantable source apparatus 62, and that some or all of the components of circuit 210 are included or otherwise coupled to the implantable receive apparatus 50/60/80/90.

The receive apparatus 50/60/80/90 is preferably configured for chronic fixation within a lumen of a renal artery 12 or on an outer wall of the renal artery 12. The source apparatus 62 is preferably configured for chronic fixation within a lumen of a renal vein 42 or on an outer wall of the renal vein 42 in proximity to the receive apparatus 50/60/80/90. The source apparatus 62 may also be located in or on the inferior vena cava 40 or elsewhere in the body in proximity to the receive apparatus 50/60/80/90. Preferably, the receive apparatus 50/60/80/90 is implemented using a stent. More preferably, the receive apparatus 50/60/80/90 and the source apparatus 62 are implemented using stents.

The transmitter electronics of the source apparatus 62 includes a microprocessor controlled switch 224/228 that creates pulsed current in a transmit antenna 206. Current is induced in a receive antenna 212 on the receive apparatus 50/60/80/90 and is rectified by rectifier 213 and stored on a capacitor 215. Denervation and/or stimulation energy output from the receive apparatus 50/60/80/90 is controlled by microprocessor 216. A DC current is delivered under the control of a microprocessor controlled switch 216/217 to the renal artery wall via an electrode arrangement 250, 260. Circuitry may be included, such as an H-bridge 263, to provide reverse polarity for charge neutralization.

Electrodes 250, 260 or other electrodes or sensors supported on or coupled to the receive apparatus 50/60/80/90 may be used to sense cardiac activity signals, such as ECG signals, through an amplifier 232 via conductor arrangement 233. In some embodiments, renal artery stimulation pulses may be synchronized with the heart rhythm and pulse, such as for renal function control therapies.

The circuitry 200 of the renal denervation and/or renal function control system shown in FIG. 16 is preferably used to controllably induce dilation of renal artery beds, but may also be used to induce dilation of artery beds other than those of the renal arteries, with or without ablation of the nerves. Ablation of the renal nerves and ganglia may be accomplished using the circuitry 200. For example, once implanted, an implantable power source (e.g., pulse generator) or a patient-external RF power source may be used to inject currents into the tissue adjacent the electrodes 250, 260 that are large enough to heat and ablate renal nerves and ganglia in or on the adventitia of the renal artery. A temperature sensor 207 of the receive circuit 210 may monitor the ablation temperature, and transmit this information to the control resource (e.g., programmer and/or operator) to control the ablation via the coil 212 or a separate antenna. As with all power and communication to the circuitry 200, the incoming energy is preferably encoded to prevent accidental stimulation from an external source.

The circuit 220 of the source apparatus 62 shown in FIG. 16 is configured as a controller/transmitter that can include a battery 226, a voltage regulator 225, and a microprocessor 224. As was discussed previously, power for the circuit 220 may be supplied by a battery of a subcutaneous medical device, such as an implantable pulse generator, stimulator, or monitor, typically positioned in a subcutaneous pocket. The inductive antenna 206 may be coupled via an electrical lead to the rest of the circuitry 220 contained in a subcutaneous medical device.

The microprocessor 224 of the source apparatus 62 may include an input-output (I/O) interface. A switch 228 can be coupled to the microprocessor 224 using the I/O interface, such as to control current flow from the battery 226 or an optional energy storage device, such as a capacitor 227, to an inductive antenna 206. In some embodiments, the inductive antenna 206 can include a wire loop inductor 208 (e.g., such as formed by multiple turns of fine wire, one or more traces or signal paths on a circuit board, or one or more other constructions). For example, the inductive antenna 206 can include multiple wire loops, at least some of which can be configured to be offset from each other or otherwise configured or arranged to generate two or more magnetic fields that can be spatially orthogonal to one another, such as to reduce orientation sensitivity of wireless energy transmission or wireless information communication using the inductive antenna 206.

A tuning element 229 can be included, such as to allow a range of frequencies to be selected at which magnetically-coupled energy 214 will be generated by the inductive antenna 206. The resulting inductance-capacitance (LC) circuit can form a resonant tank circuit, which can have an operable range of resonant frequencies selected from a range of 100 KHz to 10 MHz, but selected below the self-resonant frequency of the inductor 208 comprising the inductive antenna 206. Various embodiments of the tuning element 229 can include, but are not limited to, a capacitor, a variable-capacitance diode (e.g., "varicap" diode), an active circuit modeling a capacitor of a selected value, or the like. In some implementations, the switch 228 and the tuning element 229 can be replaced, such as by a combination of a voltage-controlled oscillator and power amplifier coupled to directly drive the inductive antenna 206, such as to generate the magnetically coupled energy 214 at a specified range of frequencies. The switch 228 can be implemented either mechanically, such as using a microminiature relay, or as solid-state device (e.g., FET, BJT, IGBT, SCR, thyristor, or the like).

In certain implementations, the regulator 225, the microprocessor 224, the sensing circuit 223, and the switch 228 can be co-integrated in a single integrated circuit or multi-chip module package. This microprocessor can include, among other elements, a microcontroller including one or more of a volatile or non-volatile memory, multiple input/output channels, an analog-to-digital converter, a power supply, a digital-to-analog converter, or one or more other circuits, modules, or components that, in an example, can be co-integrated in a single integrated circuit, a single circuit package, a multi-chip module package, a hybrid, a polyimide flex-circuit assembly, or the like.

In certain implementations, the initiation, timing, duration, or frequency range of the magnetically-coupled energy 214 can be controlled by the microprocessor 224, which can be provided with input from a sensing circuit 223. For example, the sensing circuit 223 can be coupled to one or more electrodes 205A, 205B in contact with renal artery wall tissue. The sensing circuit 223 can be coupled to one or more electrodes 204A, 204B in contact with or near cardiac tissue 202A. Sensing circuit 232 of the source circuit 220 can be configured to receive cardiac signals from one or more electrode or sensor arrangements 204A, 204B that couple to cardiac tissue or other body tissue useful for deriving cardiac activity information. For example, ECG signals can be coupled to the sensing circuit 232 and fed to the stimulus control logic 216 for synchronizing renal artery stimulation pulses with the heart rhythm and/or pulse, such as for renal function control therapies.

According to some embodiments, the source circuit 62 can be external to the body, and the electrodes 204A, 204B (and/or other electrodes) can be coupled to the skin of the patient (e.g., to measure an electrocardiogram). In other embodiments, the source circuit 62 can be included in an implantable cardiac rhythm management device, or one or more other implantable electronic units, that can include one or more sense electrodes 222A, 222B coupled to the sensing circuit 223. For example, one or more of the sense electrodes 222A, 222B can be disposed on the housing of the controller/transmitter 220. In another example, the controller/transmitter 220 can include an arrhythmia detector (such as using the microprocessor 224) configured to use information provided by the one or more sense electrodes 222A, 222B or other sensing information for detecting an arrhythmia. Sensing elements 232 and 233 may be used to sense physiologic information at the receiving apparatus 50/60/80/90, such as blood pressure in the renal artery, where this information is transmitted back to sensing element 223 through the wireless link 214B or a separate communication link. Such information can be used, for example, to control one or more wireless electrostimulation electrode assemblies 210, such as to provide coordinated electrostimulation to control or moderate renal functions for both left and right renal arteries 12 of a patient. The magnetically-coupled energy 214 can be generated for either or both wireless electrostimulation electrode assemblies 210 transferring the operating or electrostimulation energy 214A to the wireless electrostimulation electrode assembly 210, or information communication 214B with the wireless electrostimulation electrode assembly 210.

According to various embodiments, a first range of frequencies can be established for wireless energy transfer, and a second range of frequencies can be established for commanding the wireless electrostimulation electrode assembly 210 to deliver an electrostimulus. In the illustrative example shown in FIG. 16, a filter 209 can be configured to discriminate between the operating energy 214A and the information communication 214B. For example, the filter 209 can be configured to detect a particular range of frequencies included in the communication 214B captured by the wireless electrostimulation electrode assembly 210, such as by using an inductive pickup 212.

The filter 209 can be coupled to stimulus control logic 216. In certain embodiments, the logic 216 can be configured to inhibit or to initiate renal tissue electrostimulation, such as in response to the filter 209 detecting one or more specified signals. The filter 209 can include, in certain implementations, a band-pass filter, which can be coupled to a threshold comparator. In other implementations, the filter 209 can include a digital demodulator. For example, communication 214B can be encoded digitally and can include (or be transmitted concurrently to) operating energy 214A being wirelessly communicated to the wireless electrostimulation electrode assembly 210. Examples of digital encoding of communication 214B can include, but are not limited to, on-off keying, amplitude-shift keying, phase-shift keying, frequency-shift keying, or the like.

Various components, devices, and methodologies that can be adapted for use in the context of various embodiments of the invention are disclosed in commonly owned U.S. Publication No. 2009/0204170, which is previously incorporated herein by reference.

Figure 17:
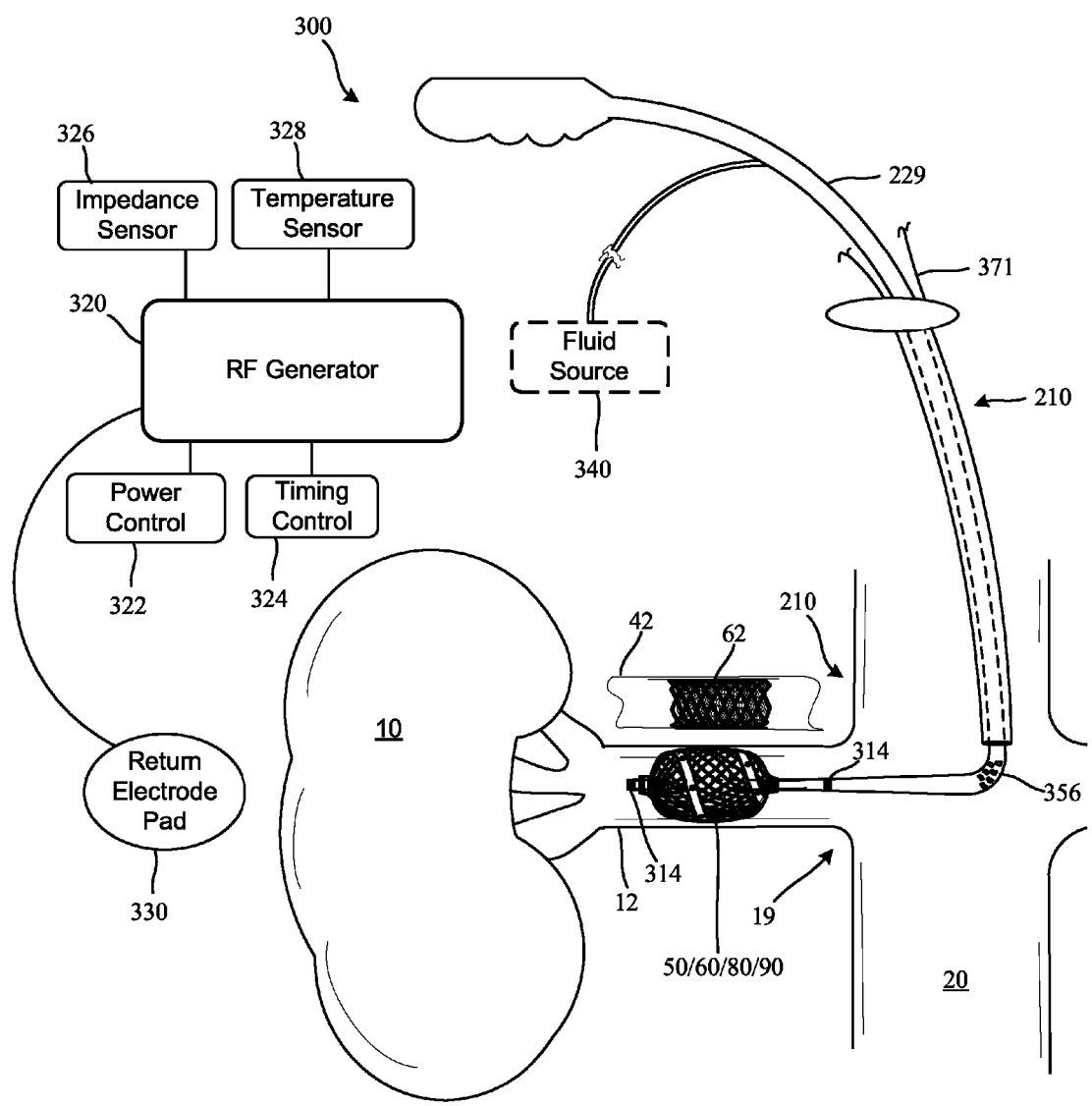
FIG. 17 shows a representative embodiment of an apparatus that can be used to implant a renal artery denervation and/or stimulation apparatus in accordance with the invention.

FIG. 17 shows a representative embodiment of an apparatus 300 that can be used to implant a renal artery denervation/stimulation apparatus 50/60/80/90 in accordance with the invention. The apparatus 300 can also be used to implant a renal vein source apparatus 62 in accordance with embodiments of the invention. According to embodiments that employ an implantable medical device having a battery (e.g., pulse generator), the battery can be connected to the renal vein source apparatus 62 via an electrical lead. After implanting one or both of the renal artery denervation/stimulation apparatus 50/60/80/90 and renal vein source apparatus 62, the apparatus 300 can be removed from the patient's body.

According to various embodiments, the apparatus 300 illustrated in FIG. 17 includes an RF generator 320 which is shown to include power control circuitry 322 and timing control circuitry 324. The RF generator 320 is also shown to include an impedance sensor 326 (optional) and temperature measuring circuitry 328. The impedance sensor 326 and temperature measuring circuitry 328 are respectively coupled to impedance and temperature sensors of the renal artery denervation/stimulation apparatus 50/60/80/90.

The RF generator 320 may include a return pad electrode 330 that is configured to comfortably engage the patient's back or other portion of the body near the kidneys for operating in a monopolar mode. According to embodiments that do not include a renal vein source apparatus 62, RF energy produced by the RF generator 320 is coupled to the renal artery denervation/stimulation apparatus 50/60/80/90 or to an implantable device equipped with a receiver for receiving the RF energy and a transmitter for transmitting energy wirelessly to the renal artery denervation/stimulation apparatus 50/60/80/90. In some embodiments that include a renal vein source apparatus 62, RF energy produced by the RF generator 320 can be coupled to the renal vein source apparatus 62, and renal vein source apparatus 62 wirelessly transmits energy to the renal artery denervation/stimulation apparatus 50/60/80/90.

It is understood that the RF generator system shown in FIG. 17 as a patient-external system may instead be incorporated in an implantable system as previously discussed. The implantable system may receive RF energy from a patient-external source, and energy received and/or stored by the implantable system may be transmitted to the renal vein source apparatus 62 via the RF generator 320 or via an electrical lead. The source apparatus 62 supplies energy received from the RF generator 320 or the electrical lead to the renal artery denervation/stimulation apparatus 50/60/80/90.

In general, when renal artery tissue temperatures rise above about 113° F. (50° C.), protein is permanently damaged (including those of renal nerve fibers). For example, any mammalian tissue that is heated above about 50° C. for even 1 second is killed. If heated over about 65° C., collagen denatures and tissue shrinks. If heated over about 65° C. and up to 100° C., cell walls break and oil separates from water. Above about 100° C., tissue desiccates.

Temperature sensors incorporated into the renal artery denervation/stimulation apparatus 50/60/80/90 allow continuous monitoring of renal artery tissue temperatures, and RF generator power is automatically adjusted so that the target temperatures are achieved and maintained. An impedance sensor arrangement 326 may be used to measure and monitor electrical impedance during RF denervation therapy, and the power and timing of the RF generator 320 may be moderated based on the impedance measurements.

Depending on the power applied, duration of time the energy is applied to renal vasculature, and the resistance of renal artery tissues, temperature decreases rapidly with distance from the renal artery denervation/stimulation apparatus 50/60/80/90, limiting lesion size and extent of damage to neighboring tissues. The size of the ablated area is determined largely by the size and shape of the conductive element(s) of the renal artery denervation/stimulation apparatus 50/60/80/90, the power applied, and the duration of time the energy is applied.

In accordance with embodiments for performing renal denervation using a percutaneous access system followed by chronic implant of a renal artery denervation/stimulation apparatus 50/60/80/90, the apparatus 300 of FIG. 17 may include a fluid source 340 containing a coolant or a cryogen The coolant or cryogen may be communicated from the fluid source 340 to a location proximate the renal artery denervation/stimulation apparatus 50/60/80/90 for cooling the renal artery wall during denervation. For example, the apparatus 300 can be used to deliver a cryocatheter or cryoballoon for deployment within a void of the renal artery denervation/stimulation apparatus 50/60/80/90.

Marker bands 314 can be placed on one or multiple parts of the catheter apparatus 210, 229, 371 to enable visualization during implant procedures. For example, one or more portions of the catheter 229, such as the hinge mechanism 356, may include a marker band 314. The marker bands 314 may be solid or split bands of platinum or other radiopaque metal, for example.

The hinge mechanism 356 shown in FIG. 17 may be constructed to enhance user manipulation of the catheter 229 when navigating around a nearly 90 degree turn from the abdominal aorta into the renal artery. It is understood that one or more hinge mechanisms 356 may be built into other catheters and sheaths that may be used to facilitate access to the renal artery via the abdominal aorta.

The shaft of the catheter 229 may be formed to include an elongate core member and a tubular member disposed about a portion of the core member. The tubular member may have a plurality of slots formed therein. The slotted hinge region 356 of the catheter's shaft may be configured to have a preferential bending direction. Details of useful hinge arrangements that can be incorporated into embodiments of a catheter 229 of the invention or other component that facilitates access to the renal artery/vein from the abdominal aorta/ inferior vena cava are disclosed in U.S. Patent Publication Nos. 2008/0021408 and 2009/0043372, which are incorporated herein by reference. It is noted that the catheter 229 may incorporate a steering mechanism in addition to, or exclusion of, a hinge arrangement 356. Known steering mechanisms incorporated into steerable guide catheters may be incorporated in various embodiments of a catheter 229 of the present invention.

The discussion provided herein concerning degrees of induced renal nerve damage, temperature ranges, amount of energy delivered into target tissue, and other embodiment details presented in this disclosure are provided for non-limiting illustrative purposes. Actual therapeutic parameters associated with the denervation and renal stimulation apparatuses and methodologies may vary somewhat or significantly from those described herein, and be impacted by a number of factors, including patient-specific factors (e.g., the patient's unique renal vasculature and sympathetic nervous system characteristics), refractoriness to drugs impacting renal function, type and technology of the therapy device(s), therapy duration and frequency, use of a single therapy device or multiplicity of therapy devices (in sequential or concurrent use), structural characteristics of the therapy device(s) employed, and other implementation and physiologic particulars, among others.

The foregoing description of the various embodiments of the invention has been presented for the purposes of illustration and description. It is not intended to be exhaustive or to limit the invention to the precise form disclosed. Many modifications and variations are possible in light of the above teaching. For example, the devices and techniques disclosed herein may be employed in vasculature of the body other than renal vasculature, such as coronary and peripheral vessels and structures. It is intended that the scope of the invention be limited not by this detailed description, but rather by the claims appended hereto.

What is claimed is:

1. An apparatus for delivering a therapy to a renal artery of a patient, comprising:
a support structure dimensioned for deployment at the renal artery, the support structure configured for chronic fixation at the renal artery;
a thermal transfer arrangement supported by the support structure and comprising one or more thermoelectric elements configured to thermally couple to the renal artery and capable of operating in at least one of a hyperthermic configuration and a hypothermic configuration;
power circuitry supported by the support structure and coupled to the thermal transfer arrangement, the power circuit comprising a receiver configured to receive energy from a power source external of the renal artery, the power source supplying energy to the receiver other than by way of a percutaneous lead; and
a control circuit supported by the support structure and coupled to the power circuitry, wherein the control circuit, if in the hyperthermic configuration, is configured to coordinate delivery of hyperthermic ablation therapy to ablate innervated renal nerve tissue at or proximate the renal artery and, if in the hyporthermic configuration, is configured to coordinate delivery of hypothermic ablation therapy to freeze innervated renal nerve tissue at or proximate the renal artery.

2. The apparatus of claim 1, wherein one or more of the thermoelectric elements are configured to operate in a hypothermic configuration and situated on the thermal transfer arrangement to cool non-targeted tissues of the renal artery.

3. The apparatus of claim 1, wherein the control circuit is configured to deliver one or both of a sequence of freeze/thaw therapy cycles and a sequence of freeze/thaw/heat therapy cycles.

4. The apparatus of claim 1, wherein the control circuit, in a monitoring configuration in which hypothermic and hypothermic therapy delivery are suspended, coordinates monitoring of at least one physiologic parameter that facilitates detection of renal sympathetic nerve activity associated with re-innervation of the renal artery.

5. The apparatus of claim 1, wherein the one or more thermoelectric elements comprise solid-state thermoelectric elements.

6. The apparatus of claim 1, wherein the support structure is configured for intravascular chronic deployment within the renal artery.

7. The apparatus of claim 1, wherein the support structure is configured for extravascular chronic deployment at the renal artery.

8. The apparatus of claim 1, wherein the power source comprises a power source external of the patient or an implantable power source.

9. The apparatus of claim 1, wherein the power source comprises:
- an implantable structure configured for deployment within a renal vein at a renal vein location proximate a location of the support structure within the renal artery; and
- a transmitter supported by the implantable structure and configured to transmit energy to the receiver.

10. The apparatus of claim 1, wherein the implantable structure comprises a stent.

11. The apparatus of claim 1, comprising a sensing circuit configured for sensing cardiac activity and supported by the support structure, the controller configured to control transfer of thermal energy to the renal artery wall via the thermal transfer arrangement in synchrony with sensed cardiac events.

12. A method for delivering a therapy to a renal artery of a patient, comprising:
- receiving energy by a receiver supported by a support structure adapted for chronic fixation within the renal artery from a power source external of the renal artery;
- communicating the energy received by the receiver to a power circuit supported by the support structure;
- supplying power from the power circuit to a thermal transfer arrangement supported by the support structure and comprising one or more thermoelectric elements configured to thermally couple to the renal artery; and
- operating the receiver and the power circuit in at least one of:
  - a hyperthermic configuration for delivering a hyperthermic therapy to ablate innervated renal nerve tissue at or proximate the renal artery; and
  - a hypothermic configuration for delivering a hypothermic therapy to freeze innervated renal nerve tissue at or proximate the renal artery;
- wherein the power source supplies energy to the receiver other than by way of a percutaneous electrical lead.

13. The method of claim 12, wherein operating the receiver and the power circuit comprises operating the receiver and the power circuit to deliver one or both of a sequence of freeze/thaw therapy cycles and a sequence of freeze/thaw/heat therapy cycles.

* * * * *